US008419638B2

(12) United States Patent  (10) Patent No.: US 8,419,638 B2
Arne et al.  (45) Date of Patent: Apr. 16, 2013

(54) BODY-ASSOCIATED FLUID TRANSPORT STRUCTURE EVALUATION DEVICES

(75) Inventors: Lawrence W. Arne, Redwood City, CA (US); Olivier Colliou, Los Gatos, CA (US); Marc Jensen, Los Gatos, CA (US); Mark Zdeblick, Portola Valley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 747 days.

(21) Appl. No.: 12/273,503

(22) Filed: Nov. 18, 2008

(65) Prior Publication Data

US 2009/0131767 A1 May 21, 2009

Related U.S. Application Data

(60) Provisional application No. 60/989,078, filed on Nov. 19, 2007.

(51) Int. Cl.
A61B 5/00 (2006.01)
(52) U.S. Cl.
USPC .......................................................... 600/301
(58) Field of Classification Search ............ 600/301
See application file for complete search history.

(56) References Cited

U.S. PATENT DOCUMENTS

| | | |
|---|---|---|
| 3,812,854 A | 5/1974 | Michaels et al. |
| 3,880,146 A | 4/1975 | Everett et al. |
| 4,403,989 A | 9/1983 | Christensen et al. |
| 4,475,905 A | 10/1984 | Himmelstrup |
| 4,487,602 A | 12/1984 | Christensen et al. |
| 4,529,401 A | 7/1985 | Leslie et al. |
| 4,551,133 A | 11/1985 | Zegers de Beyl et al. |
| 4,621,644 A | 11/1986 | Eilers |
| 4,669,479 A | 6/1987 | Dunseath, Jr. |
| 4,705,503 A | 11/1987 | Dorman et al. |
| 4,795,429 A | 1/1989 | Feldstein |
| 4,850,967 A | 7/1989 | Cosmai |
| 4,911,916 A | 3/1990 | Cleary |
| 4,922,901 A | 5/1990 | Brooks et al. |
| 5,006,342 A | 4/1991 | Cleary et al. |
| 5,125,888 A | 6/1992 | Howard et al. |
| 5,135,479 A | 8/1992 | Sibalis et al. |
| 5,156,911 A | 10/1992 | Stewart |
| 5,167,649 A | 12/1992 | Zook |
| 5,190,522 A | 3/1993 | Wojcicki et al. |
| 5,205,292 A | 4/1993 | Czar et al. |
| 5,213,568 A | 5/1993 | Lattin et al. |
| 5,246,418 A | 9/1993 | Haynes et al. |
| 5,284,133 A | 2/1994 | Burns et al. |
| 5,300,299 A | 4/1994 | Sweet et al. |
| 5,317,506 A | 5/1994 | Coutre et al. |
| 5,331,953 A | 7/1994 | Andersson et al. |
| 5,351,695 A | 10/1994 | Mills et al. |
| 5,363,842 A | 11/1994 | Mishelevich et al. |
| 5,364,838 A | 11/1994 | Rubsamen |
| 5,394,866 A | 3/1995 | Ritson et al. |
| 5,404,871 A | 4/1995 | Goodman et al. |
| 5,415,866 A | 5/1995 | Zook |
| 5,423,750 A | 6/1995 | Spiller |
| 5,479,920 A | 1/1996 | Piper et al. |
| 5,487,378 A | 1/1996 | Robertson et al. |
| 5,505,195 A | 4/1996 | Wolf |
| 5,505,958 A | 4/1996 | Bello et al. |
| 5,507,277 A | 4/1996 | Rubsamen et al. |
| 5,509,404 A | 4/1996 | Lloyd et al. |
| 5,522,378 A | 6/1996 | Ritson et al. |
| 5,527,288 A | 6/1996 | Gross et al. |
| 5,536,503 A | 7/1996 | Kitchell et al. |
| 5,540,669 A | 7/1996 | Sage et al. |
| 5,542,410 A | 8/1996 | Goodman et al. |
| 5,556,421 A | 9/1996 | Prutchi et al. |
| 5,570,682 A | 11/1996 | Johnson |
| 5,586,550 A | 12/1996 | Ivri et al. |
| 5,587,237 A | 12/1996 | Korpman |
| 5,593,390 A | 1/1997 | Castellano et al. |
| RE35,474 E | 3/1997 | Woodard et al. |
| 5,608,647 A | 3/1997 | Rubsamen et al. |
| 5,616,124 A | 4/1997 | Hague et al. |

(Continued)

FOREIGN PATENT DOCUMENTS

| | | |
|---|---|---|
| JP | 6296633 | 10/1994 |
| JP | 2001-061799 | 3/2001 |

(Continued)

OTHER PUBLICATIONS

Nikander et al., "The Adaptive Delivery System in a Telehealth Setting: Patient Acceptance, Performance and Feasibility" Journal of Aerosol Medicine and Pulmonary Drug Delivery; vol. 23, Supp. 1, (2010) pp. S21-S27.

(Continued)

*Primary Examiner* — Jerry Lin
(74) *Attorney, Agent, or Firm* — Bozicevic, Field & Francis LLP; Bret E. Field

(57) ABSTRACT

Implantable devices for evaluating body-associated fluid transport structures and methods for using the same are provided. In some instances, the implantable devices include an elongated structure with at least one hermetically sealed integrated circuit sensor stably associated therewith and a transmitter. The devices find use in a variety of different applications, including monitoring the function of various types of body-associated fluid transport structures, such as arteriovenous fistulae, vascular grafts, catheters, cerebrospinal fluid shunts, and implantable central venous access devices.

17 Claims, 8 Drawing Sheets

U.S. PATENT DOCUMENTS

| | | |
|---|---|---|
| 5,622,162 A | 4/1997 | Johansson et al. |
| 5,622,180 A | 4/1997 | Tammi et al. |
| 5,634,899 A | 6/1997 | Shapland et al. |
| 5,645,855 A | 7/1997 | Lorenz |
| 5,655,516 A | 8/1997 | Goodman et al. |
| 5,655,523 A | 8/1997 | Hodson et al. |
| 5,656,286 A | 8/1997 | Miranda et al. |
| 5,666,945 A | 9/1997 | Davenport |
| 5,676,129 A | 10/1997 | Rocci, Jr. et al. |
| 5,686,099 A | 11/1997 | Sablotsky et al. |
| 5,688,232 A | 11/1997 | Flower |
| 5,694,919 A | 12/1997 | Rubsamen et al. |
| 5,694,920 A | 12/1997 | Abrams et al. |
| 5,697,899 A | 12/1997 | Hillman et al. |
| 5,709,202 A | 1/1998 | Lloyd et al. |
| 5,713,349 A | 2/1998 | Keaney |
| 5,724,986 A | 3/1998 | Jones, Jr. et al. |
| 5,740,793 A | 4/1998 | Hodson et al. |
| 5,746,711 A | 5/1998 | Sibalis et al. |
| 5,781,442 A | 7/1998 | Engleson et al. |
| 5,794,612 A | 8/1998 | Wachter et al. |
| 5,807,375 A | 9/1998 | Gross et al. |
| 5,809,997 A | 9/1998 | Wolf |
| 5,810,888 A | 9/1998 | Fenn |
| 5,813,397 A | 9/1998 | Goodman et al. |
| 5,823,179 A | 10/1998 | Grychowski et al. |
| 5,826,570 A | 10/1998 | Goodman et al. |
| 5,830,175 A | 11/1998 | Flower |
| 5,839,430 A | 11/1998 | Cama |
| 5,843,014 A | 12/1998 | Lattin et al. |
| 5,848,991 A | 12/1998 | Gross et al. |
| 5,851,197 A | 12/1998 | Marano et al. |
| 5,857,994 A | 1/1999 | Flower |
| 5,860,957 A | 1/1999 | Jacobsen et al. |
| 5,865,786 A | 2/1999 | Sibalis et al. |
| 5,865,787 A | 2/1999 | Shapland et al. |
| 5,873,835 A | 2/1999 | Hastings et al. |
| 5,894,841 A | 4/1999 | Voges |
| 5,906,579 A | 5/1999 | Vander Salm et al. |
| 5,906,597 A | 5/1999 | McPhee |
| 5,921,237 A | 7/1999 | Eisele et al. |
| 5,924,997 A | 7/1999 | Campbell |
| 5,925,021 A | 7/1999 | Castellano et al. |
| 5,928,201 A | 7/1999 | Poulsen et al. |
| 5,960,792 A | 10/1999 | Lloyd et al. |
| 5,967,986 A | 10/1999 | Cimochowski et al. |
| 5,967,989 A | 10/1999 | Cimochowski et al. |
| 5,991,655 A | 11/1999 | Gross et al. |
| 5,997,501 A | 12/1999 | Gross et al. |
| 6,006,747 A | 12/1999 | Eisele et al. |
| 6,012,454 A | 1/2000 | Hodson et al. |
| 6,018,680 A | 1/2000 | Flower |
| 6,024,976 A | 2/2000 | Miranda et al. |
| 6,029,083 A | 2/2000 | Flower et al. |
| 6,053,873 A | 4/2000 | Govari et al. |
| 6,053,888 A | 4/2000 | Kong |
| 6,055,980 A | 5/2000 | Mecikalski et al. |
| RE36,754 E | 6/2000 | Noel |
| 6,076,519 A | 6/2000 | Johnson |
| 6,085,740 A | 7/2000 | Ivri et al. |
| 6,085,742 A | 7/2000 | Wachter |
| 6,095,141 A | 8/2000 | Armer et al. |
| 6,105,571 A | 8/2000 | Coffee |
| 6,109,260 A | 8/2000 | Bathe |
| 6,116,233 A | 9/2000 | Denyer et al. |
| 6,119,684 A | 9/2000 | Nohl et al. |
| 6,125,844 A | 10/2000 | Samiotes |
| 6,142,146 A | 11/2000 | Abrams et al. |
| 6,148,815 A | 11/2000 | Wolf |
| 6,152,130 A | 11/2000 | Abrams et al. |
| 6,196,218 B1 | 3/2001 | Voges |
| 6,196,219 B1 | 3/2001 | Hess et al. |
| 6,198,966 B1 | 3/2001 | Heruth |
| 6,202,642 B1 | 3/2001 | Mckinnon et al. |
| 6,221,383 B1 | 4/2001 | Miranda et al. |
| 6,231,560 B1 | 5/2001 | Bui et al. |
| 6,237,398 B1 | 5/2001 | Porat et al. |
| 6,237,589 B1 | 5/2001 | Denyer et al. |
| 6,237,594 B1 | 5/2001 | Davenport |
| 6,245,026 B1 | 6/2001 | Campbell et al. |
| 6,251,079 B1 | 6/2001 | Gambale et al. |
| 6,254,573 B1 | 7/2001 | Haim et al. |
| 6,256,533 B1 | 7/2001 | Yuzhakov et al. |
| 6,260,549 B1 | 7/2001 | Sosiak |
| 6,269,340 B1 | 7/2001 | Ford et al. |
| 6,272,370 B1 | 8/2001 | Gillies et al. |
| 6,283,951 B1 | 9/2001 | Flaherty et al. |
| 6,283,953 B1 | 9/2001 | Ayer et al. |
| 6,309,370 B1 | 10/2001 | Haim et al. |
| 6,315,719 B1 | 11/2001 | Rode et al. |
| 6,316,022 B1 | 11/2001 | Mantelle |
| 6,318,361 B1 | 11/2001 | Sosiak |
| 6,327,486 B1 | 12/2001 | Nissila et al. |
| 6,340,357 B1 | 1/2002 | Poulsen et al. |
| 6,349,724 B1 | 2/2002 | Burton et al. |
| 6,352,715 B1 | 3/2002 | Hwang et al. |
| 6,377,848 B1 | 4/2002 | Garde et al. |
| 6,378,520 B1 | 4/2002 | Davenport |
| 6,385,488 B1 | 5/2002 | Flower et al. |
| 6,390,088 B1 | 5/2002 | Nohl et al. |
| 6,394,997 B1 | 5/2002 | Lemelson |
| 6,397,838 B1 | 6/2002 | Zimlich et al. |
| 6,406,426 B1 | 6/2002 | Reuss et al. |
| 6,413,238 B1 | 7/2002 | Maget |
| 6,422,236 B1 | 7/2002 | Nilsson |
| 6,425,392 B1 | 7/2002 | Sosiak |
| 6,427,684 B2 | 8/2002 | Ritsche et al. |
| 6,431,171 B1 | 8/2002 | Burton |
| 6,435,175 B1 | 8/2002 | Stenzler |
| 6,443,146 B1 | 9/2002 | Voges |
| 6,448,303 B1 | 9/2002 | Paul |
| 6,453,195 B1 | 9/2002 | Thompson |
| 6,468,242 B1 | 10/2002 | Wilson et al. |
| 6,484,721 B1 | 11/2002 | Bliss |
| 6,485,461 B1 | 11/2002 | Mason et al. |
| 6,516,796 B1 | 2/2003 | Cox et al. |
| 6,517,481 B2 | 2/2003 | Hoek et al. |
| 6,517,527 B2 | 2/2003 | Gambale et al. |
| 6,520,928 B1 | 2/2003 | Junior et al. |
| 6,527,759 B1 | 3/2003 | Tachibana et al. |
| 6,533,733 B1 | 3/2003 | Ericson et al. |
| 6,536,423 B2 | 3/2003 | Conway |
| 6,540,154 B1 | 4/2003 | Ivri et al. |
| 6,564,093 B1 | 5/2003 | Ostrow et al. |
| 6,568,390 B2 | 5/2003 | Nichols et al. |
| 6,575,932 B1 | 6/2003 | O'Brien et al. |
| 6,578,741 B2 | 6/2003 | Ritsche et al. |
| 6,582,393 B2 | 6/2003 | Sage |
| 6,584,971 B1 | 7/2003 | Denyer et al. |
| 6,585,698 B1 | 7/2003 | Packman et al. |
| 6,589,229 B1 | 7/2003 | Connelly et al. |
| 6,599,281 B1 | 7/2003 | Struys et al. |
| 6,605,072 B2 | 8/2003 | Struys et al. |
| 6,606,989 B1 | 8/2003 | Brand et al. |
| 6,607,508 B2 | 8/2003 | Knauer |
| 6,615,827 B2 | 9/2003 | Greenwood et al. |
| 6,629,524 B1 | 10/2003 | Goodall et al. |
| 6,640,804 B2 | 11/2003 | Ivri et al. |
| 6,651,651 B1 | 11/2003 | Bonney et al. |
| 6,655,381 B2 | 12/2003 | Keane et al. |
| 6,656,148 B2 | 12/2003 | Das et al. |
| 6,678,555 B2 | 1/2004 | Flower et al. |
| 6,685,648 B2 | 2/2004 | Flaherty et al. |
| 6,705,316 B2 | 3/2004 | Blythe et al. |
| 6,715,487 B2 | 4/2004 | Nichols et al. |
| 6,723,077 B2 | 4/2004 | Pickup et al. |
| 6,726,661 B2 | 4/2004 | Munk et al. |
| 6,728,574 B2 | 4/2004 | Ujhelyi et al. |
| 6,745,761 B2 | 6/2004 | Christrup et al. |
| 6,745,764 B2 | 6/2004 | Hickle |
| 6,746,429 B2 | 6/2004 | Sadowski et al. |
| 6,748,945 B2 | 6/2004 | Grychowski et al. |
| 6,796,305 B1 | 9/2004 | Banner et al. |
| 6,796,956 B2 | 9/2004 | Hartlaub et al. |
| 6,807,965 B1 | 10/2004 | Hickle |
| 6,810,290 B2 | 10/2004 | Lebel et al. |
| 6,854,461 B2 | 2/2005 | Nichols et al. |

| Patent | Kind | Date | Inventor |
|---|---|---|---|
| 6,858,011 | B2 | 2/2005 | Sehgal |
| 6,866,037 | B1 | 3/2005 | Aslin et al. |
| 6,886,557 | B2 | 5/2005 | Childers et al. |
| 6,893,415 | B2 | 5/2005 | Madsen et al. |
| 6,902,740 | B2 | 6/2005 | Schaberg et al. |
| 6,923,784 | B2 | 8/2005 | Stein et al. |
| 6,941,168 | B2 | 9/2005 | Girouard et al. |
| 6,949,081 | B1 | 9/2005 | Chance |
| 6,958,691 | B1 | 10/2005 | Anderson et al. |
| 6,961,601 | B2 | 11/2005 | Matthews et al. |
| 6,971,383 | B2 | 12/2005 | Hickey et al. |
| 6,981,499 | B2 | 1/2006 | Anderson et al. |
| 6,983,652 | B2 | 1/2006 | Blakley et al. |
| 6,985,771 | B2 | 1/2006 | Fischell et al. |
| 6,985,870 | B2 | 1/2006 | Martucci et al. |
| 6,990,975 | B1 | 1/2006 | Jones et al. |
| 6,999,854 | B2 | 2/2006 | Roth |
| 7,010,337 | B2 | 3/2006 | Furnary et al. |
| 7,034,692 | B2 | 4/2006 | Hickle |
| 7,040,314 | B2 | 5/2006 | Nguyen et al. |
| 7,044,911 | B2 | 5/2006 | Drinan et al. |
| 7,047,964 | B2 | 5/2006 | Bacon |
| 7,054,782 | B2 | 5/2006 | Hartlaub |
| 7,072,802 | B2 | 7/2006 | Hartlaub |
| 7,089,935 | B1 | 8/2006 | Rand |
| 7,097,853 | B1 | 8/2006 | Garbe et al. |
| 7,104,972 | B2 | 9/2006 | Moller et al. |
| 7,107,988 | B2 | 9/2006 | Pinon et al. |
| 7,108,680 | B2 | 9/2006 | Rohr et al. |
| 7,117,867 | B2 | 10/2006 | Cox et al. |
| 7,138,088 | B2 | 11/2006 | Wariar et al. |
| 7,147,170 | B2 | 12/2006 | Nguyen et al. |
| 7,168,597 | B1 | 1/2007 | Jones et al. |
| 7,181,261 | B2 | 2/2007 | Silver et al. |
| 7,191,777 | B2 | 3/2007 | Brand et al. |
| 7,198,172 | B2 | 4/2007 | Harvey et al. |
| 7,201,734 | B2 | 4/2007 | Hickle |
| 7,204,823 | B2 | 4/2007 | Estes et al. |
| 7,220,240 | B2 | 5/2007 | Struys et al. |
| 7,225,805 | B2 | 6/2007 | Bacon |
| 7,232,435 | B2 | 6/2007 | Hildebrand et al. |
| 7,242,981 | B2 | 7/2007 | Ginggen |
| 7,247,154 | B2 | 7/2007 | Hickle |
| 7,261,733 | B1 | 8/2007 | Brown et al. |
| 7,267,121 | B2 | 9/2007 | Ivri et al. |
| 7,278,983 | B2 | 10/2007 | Ireland et al. |
| 7,291,126 | B2 | 11/2007 | Shekalim |
| 7,320,675 | B2 | 1/2008 | Pastore et al. |
| 7,322,352 | B2 | 1/2008 | Minshull et al. |
| 7,322,355 | B2 | 1/2008 | Jones et al. |
| 7,331,340 | B2 | 2/2008 | Barney |
| 7,342,660 | B2 | 3/2008 | Altobelli et al. |
| 7,347,200 | B2 | 3/2008 | Jones et al. |
| 7,347,202 | B2 | 3/2008 | Aslin et al. |
| 7,347,851 | B1 | 3/2008 | Kriksunov |
| 7,367,968 | B2 | 5/2008 | Rosenberg et al. |
| 7,380,550 | B2 | 6/2008 | Sexton et al. |
| 7,382,263 | B2 | 6/2008 | Danowski et al. |
| 7,383,837 | B2 | 6/2008 | Robertson et al. |
| 7,387,121 | B2 | 6/2008 | Harvey |
| 7,390,311 | B2 | 6/2008 | Hildebrand et al. |
| 7,397,730 | B2 | 7/2008 | Skyggebjerg et al. |
| 7,415,384 | B2 | 8/2008 | Hartlaub |
| 7,424,888 | B2 | 9/2008 | Harvey et al. |
| 7,455,667 | B2 | 11/2008 | Uhland et al. |
| 7,458,373 | B2 | 12/2008 | Nichols et al. |
| 7,467,629 | B2 | 12/2008 | Rand |
| 7,483,743 | B2 | 1/2009 | Mann et al. |
| 7,488,305 | B2 | 2/2009 | Mickley et al. |
| 7,495,546 | B2 | 2/2009 | Lintell et al. |
| 7,510,551 | B2 | 3/2009 | Uhland et al. |
| 7,517,332 | B2 | 4/2009 | Tonelli et al. |
| 7,520,278 | B2 | 4/2009 | Crowder et al. |
| 7,530,352 | B2 | 5/2009 | Childers et al. |
| 7,530,975 | B2 | 5/2009 | Hunter |
| 7,537,590 | B2 | 5/2009 | Santini et al. |
| 7,542,798 | B2 | 6/2009 | Girouard |
| 7,544,190 | B2 | 6/2009 | Pickup et al. |
| 7,548,314 | B2 | 6/2009 | Altobelli et al. |
| 7,549,421 | B2 | 6/2009 | Levi et al. |
| 7,552,728 | B2 | 6/2009 | Bonney et al. |
| 7,554,090 | B2 | 6/2009 | Coleman et al. |
| 7,575,003 | B2 | 8/2009 | Rasmussen et al. |
| 7,581,540 | B2 | 9/2009 | Hale et al. |
| 7,597,099 | B2 | 10/2009 | Jones et al. |
| 7,631,643 | B2 | 12/2009 | Morrison et al. |
| 7,670,329 | B2 | 3/2010 | Flaherty et al. |
| 7,672,726 | B2 | 3/2010 | Ginggen |
| 7,677,467 | B2 | 3/2010 | Fink et al. |
| 7,686,788 | B2 | 3/2010 | Freyman et al. |
| 7,699,060 | B2 | 4/2010 | Behm |
| 7,699,829 | B2 | 4/2010 | Harris et al. |
| 7,708,011 | B2 | 5/2010 | Hochrainer et al. |
| 7,713,229 | B2 | 5/2010 | Veit et al. |
| 7,715,919 | B2 | 5/2010 | Osorio et al. |
| 7,717,877 | B2 | 5/2010 | Lavi et al. |
| 7,725,161 | B2 | 5/2010 | Karmarkar et al. |
| 7,783,344 | B2 | 8/2010 | Lackey et al. |
| 7,909,790 | B2 * | 3/2011 | Burnett ............... 604/9 |
| 2001/0000802 | A1 | 5/2001 | Soykan et al. |
| 2001/0022279 | A1 | 9/2001 | Denyer et al. |
| 2002/0000225 | A1 | 1/2002 | Schuler et al. |
| 2002/0002349 | A1 | 1/2002 | Flaherty et al. |
| 2002/0010432 | A1 | 1/2002 | Klitmose |
| 2002/0013615 | A1 | 1/2002 | Haim et al. |
| 2002/0026940 | A1 | 3/2002 | Brooker et al. |
| 2002/0077852 | A1 | 6/2002 | Ford et al. |
| 2002/0099328 | A1 | 7/2002 | Scheiner et al. |
| 2002/0120236 | A1 | 8/2002 | Diaz et al. |
| 2002/0153006 | A1 | 10/2002 | Zimlich et al. |
| 2002/0189612 | A1 | 12/2002 | Rand et al. |
| 2002/0189615 | A1 | 12/2002 | Henry et al. |
| 2002/0198493 | A1 | 12/2002 | Diaz et al. |
| 2003/0004236 | A1 | 1/2003 | Meade et al. |
| 2003/0078561 | A1 | 4/2003 | Gambale et al. |
| 2003/0079744 | A1 | 5/2003 | Bonney et al. |
| 2003/0094508 | A1 | 5/2003 | Peng et al. |
| 2003/0136418 | A1 | 7/2003 | Behm et al. |
| 2003/0140921 | A1 | 7/2003 | Smith et al. |
| 2003/0150446 | A1 | 8/2003 | Patel et al. |
| 2003/0159693 | A1 | 8/2003 | Melker et al. |
| 2003/0168057 | A1 | 9/2003 | Snyder et al. |
| 2003/0171738 | A1 | 9/2003 | Konieczynski et al. |
| 2003/0176804 | A1 | 9/2003 | Melker et al. |
| 2003/0183226 | A1 | 10/2003 | Brand et al. |
| 2003/0205229 | A1 | 11/2003 | Crockford et al. |
| 2004/0004133 | A1 | 1/2004 | Ivri et al. |
| 2004/0019321 | A1 | 1/2004 | Sage et al. |
| 2004/0025871 | A1 | 2/2004 | Davies et al. |
| 2004/0031331 | A1 | 2/2004 | Blakley et al. |
| 2004/0050385 | A1 | 3/2004 | Bonney et al. |
| 2004/0089299 | A1 | 5/2004 | Bonney et al. |
| 2004/0098117 | A1 | 5/2004 | Hossainy et al. |
| 2004/0106902 | A1 | 6/2004 | Diaz et al. |
| 2004/0122530 | A1 | 6/2004 | Hansen et al. |
| 2004/0133154 | A1 | 7/2004 | Flaherty et al. |
| 2004/0139963 | A1 | 7/2004 | Ivri et al. |
| 2004/0158167 | A1 | 8/2004 | Smith et al. |
| 2004/0181196 | A1 | 9/2004 | Pickup et al. |
| 2004/0187864 | A1 | 9/2004 | Adams et al. |
| 2004/0193453 | A1 | 9/2004 | Butterfield et al. |
| 2004/0210199 | A1 | 10/2004 | Atterbury et al. |
| 2004/0254435 | A1 | 12/2004 | Mathews et al. |
| 2005/0010166 | A1 | 1/2005 | Hickle |
| 2005/0045734 | A1 | 3/2005 | Peng et al. |
| 2005/0059924 | A1 | 3/2005 | Katz et al. |
| 2005/0072421 | A1 | 4/2005 | Suman et al. |
| 2005/0081845 | A1 | 4/2005 | Barney et al. |
| 2005/0087189 | A1 | 4/2005 | Crockford et al. |
| 2005/0137626 | A1 | 6/2005 | Pastore et al. |
| 2005/0139651 | A1 | 6/2005 | Lim |
| 2005/0155602 | A1 | 7/2005 | Lipp |
| 2005/0165342 | A1 | 7/2005 | Odland |
| 2005/0172956 | A1 | 8/2005 | Childers et al. |
| 2005/0172958 | A1 | 8/2005 | Singer et al. |
| 2005/0183725 | A1 | 8/2005 | Gumaste et al. |
| 2005/0203637 | A1 | 9/2005 | Edman et al. |
| 2005/0235732 | A1 | 10/2005 | Rush |

| | | | | | | |
|---|---|---|---|---|---|---|
| 2005/0236501 A1 | 10/2005 | Zimlich et al. | | 2009/0024112 A1 | 1/2009 | Edwards et al. |
| 2005/0245906 A1 | 11/2005 | Makower et al. | | 2009/0025714 A1 | 1/2009 | Denyer et al. |
| 2005/0247312 A1 | 11/2005 | Davies | | 2009/0025718 A1 | 1/2009 | Denyer et al. |
| 2005/0251289 A1 | 11/2005 | Bonney et al. | | 2009/0048526 A1 | 2/2009 | Aarts et al. |
| 2005/0274378 A1 | 12/2005 | Bonney et al. | | 2009/0048556 A1 | 2/2009 | Durand |
| 2006/0005842 A1 | 1/2006 | Rashad et al. | | 2009/0056708 A1 | 3/2009 | Stenzler |
| 2006/0030813 A1 | 2/2006 | Chance | | 2009/0064997 A1 | 3/2009 | Li |
| 2006/0031099 A1 | 2/2006 | Vitello et al. | | 2009/0082829 A1 | 3/2009 | Panken et al. |
| 2006/0037612 A1 | 2/2006 | Herder et al. | | 2009/0107503 A1 | 4/2009 | Baran |
| 2006/0042632 A1 | 3/2006 | Bishop et al. | | 2009/0151718 A1 | 6/2009 | Hunter et al. |
| 2006/0058593 A1 | 3/2006 | Drinan et al. | | 2009/0156952 A1 | 6/2009 | Hunter et al. |
| 2006/0090752 A1 | 5/2006 | Imondi et al. | | 2009/0163781 A1 | 6/2009 | Say et al. |
| 2006/0130832 A1 | 6/2006 | Schechter et al. | | 2009/0187167 A1 | 7/2009 | Sexton et al. |
| 2006/0131350 A1 | 6/2006 | Schechter et al. | | 2009/0194104 A1 | 8/2009 | Van Sickle |
| 2006/0167530 A1 | 7/2006 | Flaherty et al. | | 2009/0211576 A1 | 8/2009 | Lehtonen et al. |
| 2006/0178586 A1 | 8/2006 | Dobak | | 2009/0213373 A1 | 8/2009 | Altobelli et al. |
| 2006/0184087 A1 | 8/2006 | Wariar et al. | | 2009/0216194 A1 | 8/2009 | Elgard Pedersen et al. |
| 2006/0191534 A1 | 8/2006 | Hickey et al. | | 2009/0221087 A1 | 9/2009 | Martin et al. |
| 2006/0201499 A1 | 9/2006 | Muellinger et al. | | 2009/0227941 A1 | 9/2009 | Say et al. |
| 2006/0204532 A1 | 9/2006 | John et al. | | 2009/0229607 A1 | 9/2009 | Brunnberg et al. |
| 2006/0231093 A1 | 10/2006 | Burge et al. | | 2009/0241951 A1 | 10/2009 | Jafari et al. |
| 2006/0243277 A1 | 11/2006 | Denyer et al. | | 2009/0241955 A1 | 10/2009 | Jafari et al. |
| 2006/0253005 A1 | 11/2006 | Drinan | | 2009/0270752 A1 | 10/2009 | Coifman |
| 2006/0283465 A1 | 12/2006 | Nickel | | 2009/0301472 A1 | 12/2009 | Kim et al. |
| 2007/0023034 A1 | 2/2007 | Jongejan et al. | | 2009/0314372 A1 | 12/2009 | Ruskewicz et al. |
| 2007/0023036 A1 | 2/2007 | Grychowski et al. | | 2009/0326509 A1 | 12/2009 | Muse et al. |
| 2007/0043591 A1 | 2/2007 | Meretei et al. | | 2009/0326510 A1 | 12/2009 | Haefner et al. |
| 2007/0044793 A1 | 3/2007 | Kleinstreuer et al. | | 2010/0012120 A1 | 1/2010 | Herder et al. |
| 2007/0060800 A1 | 3/2007 | Drinan et al. | | 2010/0031957 A1 | 2/2010 | McIntosh |
| 2007/0074722 A1 | 4/2007 | Giroux et al. | | 2010/0049004 A1 | 2/2010 | Edman et al. |
| 2007/0088334 A1 | 4/2007 | Hillis et al. | | 2010/0049172 A1 | 2/2010 | Chance |
| 2007/0091273 A1 | 4/2007 | Sullivan et al. | | 2010/0078015 A1 | 4/2010 | Imran |
| 2007/0107517 A1 | 5/2007 | Arnold et al. | | 2010/0094099 A1 | 4/2010 | Levy et al. |
| 2007/0123829 A1 | 5/2007 | Atterbury et al. | | 2010/0099967 A1 | 4/2010 | Say et al. |
| 2007/0125370 A1 | 6/2007 | Denyer et al. | | 2010/0100078 A1 | 4/2010 | Say et al. |
| 2007/0157931 A1 | 7/2007 | Parker et al. | | 2010/0100160 A1 | 4/2010 | Edman et al. |
| 2007/0161879 A1 | 7/2007 | Say et al. | | 2010/0106098 A1 | 4/2010 | Atterbury et al. |
| 2007/0169778 A1 | 7/2007 | Smith et al. | | 2010/0114026 A1 | 5/2010 | Karratt et al. |
| 2007/0197954 A1 | 8/2007 | Keenan | | 2010/0114060 A1 | 5/2010 | Ginggen et al. |
| 2007/0203411 A1 | 8/2007 | Say et al. | | 2010/0116070 A1 | 5/2010 | Farina et al. |
| 2007/0208322 A1 | 9/2007 | Rantala et al. | | 2010/0121314 A1 | 5/2010 | Iobbi |
| 2007/0209659 A1 | 9/2007 | Ivri et al. | | 2010/0122697 A1 | 5/2010 | Przekwas et al. |
| 2007/0213658 A1 | 9/2007 | Hickle | | 2010/0268111 A1 | 10/2010 | Drinan et al. |
| 2007/0221218 A1 | 9/2007 | Warden et al. | | 2011/0224912 A1 | 9/2011 | Bhavaraju et al. |
| 2007/0224128 A1 | 9/2007 | Dennis et al. | | 2011/0230732 A1 | 9/2011 | Edman et al. |
| 2007/0240712 A1 | 10/2007 | Fleming et al. | | | | |
| 2007/0256688 A1 | 11/2007 | Schuster et al. | | | FOREIGN PATENT DOCUMENTS | |
| 2007/0258894 A1 | 11/2007 | Melker et al. | | JP | 2008-525063 | 7/2008 |
| 2007/0295329 A1 | 12/2007 | Lieberman et al. | | WO | WO8102982 | 10/1981 |
| 2007/0299550 A1 | 12/2007 | Nishijima et al. | | WO | WO8607269 | 12/1986 |
| 2008/0009800 A1 | 1/2008 | Nickel | | WO | WO9207599 | 5/1992 |
| 2008/0021379 A1 | 1/2008 | Hickle | | WO | WO9209324 | 6/1992 |
| 2008/0039700 A1 | 2/2008 | Drinan et al. | | WO | WO9211808 | 7/1992 |
| 2008/0051667 A1 | 2/2008 | Goldreich et al. | | WO | WO9215353 | 9/1992 |
| 2008/0058703 A1 | 3/2008 | Subramony et al. | | WO | WO9217231 | 10/1992 |
| 2008/0077080 A1 | 3/2008 | Hengstenberg et al. | | WO | WO9306803 | 4/1993 |
| 2008/0078382 A1 | 4/2008 | LeMahieu et al. | | WO | WO9312823 | 7/1993 |
| 2008/0078385 A1 | 4/2008 | Xiao et al. | | WO | WO9405359 | 3/1994 |
| 2008/0082001 A1 | 4/2008 | Hatlestad et al. | | WO | WO9408655 | 4/1994 |
| 2008/0086112 A1 | 4/2008 | Lo et al. | | WO | WO9416755 | 8/1994 |
| 2008/0091138 A1 | 4/2008 | Pastore et al. | | WO | WO9416756 | 8/1994 |
| 2008/0114299 A1 | 5/2008 | Damgaard-Sorensen et al. | | WO | WO9416759 | 8/1994 |
| 2008/0125759 A1 | 5/2008 | Konieczynski et al. | | WO | WO9427653 | 12/1994 |
| 2008/0142002 A1 | 6/2008 | Fink et al. | | WO | WO9507723 | 3/1995 |
| 2008/0147004 A1 | 6/2008 | Mann et al. | | WO | WO9507724 | 3/1995 |
| 2008/0147050 A1 | 6/2008 | Mann et al. | | WO | WO9513838 | 5/1995 |
| 2008/0173301 A1 | 7/2008 | Deaton et al. | | WO | WO9526769 | 10/1995 |
| 2008/0177246 A1 | 7/2008 | Sullivan et al. | | WO | WO9610440 | 4/1996 |
| 2008/0178872 A1 | 7/2008 | Genova et al. | | WO | WO9616686 | 6/1996 |
| 2008/0200804 A1 | 8/2008 | Hartlep et al. | | WO | WO9625186 | 8/1996 |
| 2008/0216834 A1 | 9/2008 | Easley et al. | | WO | WO9625978 | 8/1996 |
| 2008/0221408 A1 | 9/2008 | Hoarau et al. | | WO | WO9627341 | 9/1996 |
| 2008/0262469 A1 | 10/2008 | Brister et al. | | WO | WO9630078 | 10/1996 |
| 2008/0269689 A1 | 10/2008 | Edwards et al. | | WO | WO9707896 | 3/1997 |
| 2008/0281276 A1 | 11/2008 | Shekalim | | WO | WO9711655 | 4/1997 |
| 2008/0306436 A1 | 12/2008 | Edwards et al. | | WO | WO9711742 | 4/1997 |
| 2008/0306444 A1 | 12/2008 | Brister et al. | | WO | WO9711743 | 4/1997 |
| 2008/0306449 A1 | 12/2008 | Kristensen et al. | | WO | WO9726934 | 7/1997 |
| 2009/0005763 A1 | 1/2009 | Makower et al. | | WO | WO9733640 | 9/1997 |

| | | | | | | |
|---|---|---|---|---|---|---|
| WO | WO9733645 | 9/1997 | | WO | WO2004041339 | 5/2004 |
| WO | WO9748431 | 12/1997 | | WO | WO2004045690 | 6/2004 |
| WO | WO9800188 | 1/1998 | | WO | WO2004060436 | 7/2004 |
| WO | WO9801168 | 1/1998 | | WO | WO2004060443 | 7/2004 |
| WO | WO9806450 | 2/1998 | | WO | WO2004060447 | 7/2004 |
| WO | WO9814235 | 4/1998 | | WO | WO2004080522 | 9/2004 |
| WO | WO9832479 | 7/1998 | | WO | WO2004088567 | 10/2004 |
| WO | WO9839057 | 9/1998 | | WO | WO2005009514 | 2/2005 |
| WO | WO9844984 | 10/1998 | | WO | WO2005011779 | 2/2005 |
| WO | WO9850095 | 11/1998 | | WO | WO2005028008 | 3/2005 |
| WO | WO9900144 | 1/1999 | | WO | WO2005031317 | 4/2005 |
| WO | WO9930760 | 6/1999 | | WO | WO2005039750 | 5/2005 |
| WO | WO9965551 | 12/1999 | | WO | WO2005046559 | 5/2005 |
| WO | WO0001434 | 1/2000 | | WO | WO2005051177 | 6/2005 |
| WO | WO0007652 | 2/2000 | | WO | WO2005072798 | 8/2005 |
| WO | WO0018339 | 4/2000 | | WO | WO2005084275 | 9/2005 |
| WO | WO0021598 | 4/2000 | | WO | WO2005084738 | 9/2005 |
| WO | WO0027278 | 5/2000 | | WO | WO2005087299 | 9/2005 |
| WO | WO0032267 | 6/2000 | | WO | WO2005102412 | 11/2005 |
| WO | WO0038770 | 7/2000 | | WO | WO2005102417 | 11/2005 |
| WO | WO0043059 | 7/2000 | | WO | WO2005102418 | 11/2005 |
| WO | WO0047253 | 8/2000 | | WO | WO2005102428 | 11/2005 |
| WO | WO0050111 | 8/2000 | | WO | WO2005120615 | 12/2005 |
| WO | WO0053247 | 9/2000 | | WO | WO2005123002 | 12/2005 |
| WO | WO0059483 | 10/2000 | | WO | WO2006003665 | 1/2006 |
| WO | 01/05463 A1 | 1/2001 | | WO | WO2006009596 | 1/2006 |
| WO | 0105463 | 1/2001 | | WO | WO2006015299 | 2/2006 |
| WO | WO0113973 | 3/2001 | | WO | 2006029090 | 3/2006 |
| WO | WO0124851 | 4/2001 | | WO | 2006029090 A2 | 3/2006 |
| WO | WO0130419 | 5/2001 | | WO | WO2006022714 | 3/2006 |
| WO | WO0158236 | 8/2001 | | WO | WO2006023644 | 3/2006 |
| WO | WO0168169 | 9/2001 | | WO | WO2006035443 | 4/2006 |
| WO | WO0183007 | 11/2001 | | WO | WO2006044206 | 4/2006 |
| WO | WO0185027 | 11/2001 | | WO | WO2006045524 | 5/2006 |
| WO | WO0187378 | 11/2001 | | WO | 2006069323 | 6/2006 |
| WO | WO0189607 | 11/2001 | | WO | 2006069323 A1 | 6/2006 |
| WO | WO0200280 | 1/2002 | | WO | WO2006058426 | 6/2006 |
| WO | WO0202052 | 1/2002 | | WO | WO2006060106 | 6/2006 |
| WO | WO0204043 | 1/2002 | | WO | WO2006079898 | 8/2006 |
| WO | WO0217988 | 3/2002 | | WO | WO2006096286 | 9/2006 |
| WO | WO0217998 | 3/2002 | | WO | WO2006098933 | 9/2006 |
| WO | WO0224257 | 3/2002 | | WO | WO2006098936 | 9/2006 |
| WO | WO0224268 | 3/2002 | | WO | WO2006113408 | 10/2006 |
| WO | WO0234318 | 5/2002 | | WO | 2006/116718 | 11/2006 |
| WO | WO0236181 | 5/2002 | | WO | 2006116718 | 11/2006 |
| WO | WO02053223 | 7/2002 | | WO | WO2006120253 | 11/2006 |
| WO | WO02072178 | 9/2002 | | WO | WO2006124759 | 11/2006 |
| WO | WO02076533 | 10/2002 | | WO | WO2006125577 | 11/2006 |
| WO | WO02078535 | 10/2002 | | WO | WO2006127257 | 11/2006 |
| WO | WO02081016 | 10/2002 | | WO | WO2006127905 | 11/2006 |
| WO | WO02089879 | 11/2002 | | WO | WO2006127953 | 11/2006 |
| WO | WO02089884 | 11/2002 | | WO | WO2006128794 | 12/2006 |
| WO | WO02096489 | 12/2002 | | WO | WO2006130098 | 12/2006 |
| WO | WO03006091 | 1/2003 | | WO | WO2006133101 | 12/2006 |
| WO | WO03008014 | 1/2003 | | WO | WO2007012854 | 2/2007 |
| WO | WO03020349 | 3/2003 | | WO | 2007028035 | 3/2007 |
| WO | WO03022327 | 3/2003 | | WO | 2007028035 A2 | 3/2007 |
| WO | WO03028797 | 4/2003 | | WO | WO2007031740 | 3/2007 |
| WO | WO03035172 | 5/2003 | | WO | WO2007034237 | 3/2007 |
| WO | WO03038566 | 5/2003 | | WO | WO2007041158 | 4/2007 |
| WO | WO03045302 | 6/2003 | | WO | WO2007041471 | 4/2007 |
| WO | WO03059413 | 7/2003 | | WO | WO2007051563 | 5/2007 |
| WO | WO03071930 | 9/2003 | | WO | WO2007070093 | 6/2007 |
| WO | WO03073977 | 9/2003 | | WO | WO2007070695 | 6/2007 |
| WO | WO03086505 | 10/2003 | | WO | 2007120884 | 10/2007 |
| WO | WO03090821 | 11/2003 | | WO | 2007120884 A2 | 10/2007 |
| WO | WO03097120 | 11/2003 | | WO | WO2007125699 | 11/2007 |
| WO | WO2004009161 | 1/2004 | | WO | WO2007127981 | 11/2007 |
| WO | WO2004011067 | 2/2004 | | WO | WO2007131025 | 11/2007 |
| WO | WO2004012801 | 2/2004 | | WO | 2008008281 A2 | 1/2008 |
| WO | WO2004020024 | 3/2004 | | WO | WO2008008281 | 1/2008 |
| WO | WO2004021882 | 3/2004 | | WO | WO2008016698 | 2/2008 |
| WO | WO2004022128 | 3/2004 | | WO | WO2008021252 | 2/2008 |
| WO | WO2004022153 | 3/2004 | | WO | WO2008022010 | 2/2008 |
| WO | WO2004022242 | 3/2004 | | WO | WO2008029403 | 3/2008 |
| WO | WO2004026380 | 4/2004 | | WO | WO2008030837 | 3/2008 |
| WO | WO2004032989 | 4/2004 | | WO | WO2008037801 | 4/2008 |
| WO | WO2004034998 | 4/2004 | | WO | WO2008038241 | 4/2008 |
| WO | WO2004041334 | 5/2004 | | WO | WO2008039091 | 4/2008 |

| | | |
|---|---|---|
| WO | WO2008043724 | 4/2008 |
| WO | WO2008052039 | 5/2008 |
| WO | WO2008073806 | 6/2008 |
| WO | WO2008077706 | 7/2008 |
| WO | WO2008078287 | 7/2008 |
| WO | 2008/095183 | 8/2008 |
| WO | 2008095183 | 8/2008 |
| WO | WO2008103620 | 8/2008 |
| WO | WO2008115906 | 9/2008 |
| WO | WO2008117226 | 10/2008 |
| WO | WO2008127743 | 10/2008 |
| WO | WO2008130801 | 10/2008 |
| WO | WO2008134107 | 11/2008 |
| WO | WO2008134545 | 11/2008 |
| WO | WO2008152588 | 12/2008 |
| WO | WO2008154312 | 12/2008 |
| WO | WO2008154504 | 12/2008 |
| WO | WO2009003989 | 1/2009 |
| WO | WO2009008001 | 1/2009 |
| WO | WO2009013501 | 1/2009 |
| WO | WO2009013670 | 1/2009 |
| WO | WO2009023247 | 2/2009 |
| WO | WO2009035759 | 3/2009 |
| WO | WO2009042379 | 4/2009 |
| WO | WO2009049252 | 4/2009 |
| WO | WO2009063421 | 5/2009 |
| WO | WO2009072079 | 6/2009 |
| WO | WO2009076363 | 6/2009 |
| WO | WO2009079589 | 6/2009 |
| WO | WO2009081262 | 7/2009 |
| WO | WO2009091851 | 7/2009 |
| WO | WO2009098648 | 8/2009 |
| WO | WO2009105337 | 8/2009 |
| WO | WO2009126653 | 10/2009 |
| WO | WO2009137661 | 11/2009 |
| WO | WO2009140251 | 11/2009 |
| WO | WO2009145801 | 12/2009 |
| WO | WO2009155335 | 12/2009 |
| WO | WO2010007573 | 1/2010 |
| WO | WO2010007574 | 1/2010 |
| WO | WO2010008424 | 1/2010 |
| WO | WO2010010473 | 1/2010 |
| WO | WO2010021589 | 2/2010 |
| WO | WO2010023591 | 3/2010 |
| WO | WO2010025428 | 3/2010 |
| WO | WO2010025431 | 3/2010 |
| WO | WO2010029054 | 3/2010 |
| WO | WO2010037828 | 4/2010 |
| WO | WO2010042034 | 4/2010 |
| WO | WO2010043054 | 4/2010 |
| WO | WO2010045460 | 4/2010 |
| WO | WO2010051551 | 5/2010 |
| WO | WO2010052275 | 5/2010 |
| WO | WO2010062675 | 6/2010 |

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

Juvenile Diabetes Research Foundation International (JDRF), "Artificial Pancreas Project" (2010); http://www.artificialpancreasproject.com/; 3 pp.

Medtronic, "CareLink Therapy Management Software for Diabetes" (2010); https://carelink.minimed.com/patient/entry.jsp?bhcp=1; 1 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.

Park, "Medtronic to Buy MiniMed for $3.7 Billion" (2001) HomeCare; http://homecaremag.com/mag/medical_medtronic_buy_minimed/; 2 pp.

Lifescan, "OneTouch UltraLink™" http://www.lifescan.com/products/meters/ultralink (2010) 2 pp.

Medtronic, "Carelink™ USB" http://www.medtronicdiabetes.com/pdf/carelink_usb_factsheet.pdf (2008) 2pp.

Medtronic "The New MiniMed Paradigm® REAL-Time Revel™ System" http://www.medtronicdiabetes.com/products/index.html; (2010) 2 pp.

Medtronic, "Mini Med Paradigm® Revel™ Insulin Pump" http://www.medtronicdiabetes.com/products/insulinpumps/index.html; (2010) 2 pp.

Prutchi et al., "Design and Development of Medical Electronic Instrumentation: A Practical Perspective of the Design, Construction, and Test of Medical Devices" Wiley-Interscience (2005) pp. 12-14.

* cited by examiner

BODY-ASSOCIATED FLUID TRANSPORT STRUCTURE EVALUATION DEVICES

CROSS-REFERENCE TO RELATED APPLICATIONS

Pursuant to 35 U.S.C. §119 (e), this application claims priority to the filing date of the U.S. Provisional Patent Application Ser. No. 60/989,078 filed Nov. 19, 2007; the disclosure of which application is herein incorporated by reference.

INTRODUCTION

Medical fluid transport structures are important in a variety of medical treatments and conditions. Medical fluid transport structures include naturally occurring and surgically created structures, such as arteriovenous fistulae. Medical fluid transport structures also include fully synthetic structures, such as grafts, catheters and implantable central venous access devices. Specific types of fluid transport structures that find use in medical treatment protocols include, but are not limited to: cerebrospinal fluid shunts, implantable central venous access devices, arteriovenous fistulae, vascular grafts, and urinary catheters.

While implantable or surgically created fluid transport structures find use in a variety of different applications, complications with their use can arise. Examples of complications include: infection of the structure; physical compromise of the structure which may result in a decrease in or blockage of fluid flow through the structure; difficulties in locating the structure; and trauma to the structure. As such, there is a continued interest in the development of improved devices and methods for evaluating fluid flow in native, surgically created, and implantable fluid transport structures.

SUMMARY

Implantable devices for evaluating body-associated fluid transport structures and methods for using the same are provided. In some instances, the implantable devices include an elongated structure with at least one hermetically sealed integrated circuit sensor stably associated therewith and a transmitter. The devices find use in a variety of different applications, including monitoring the function of various types of body-associated fluid transport structures, such as arteriovenous fistulae, vascular grafts, catheters, cerebrospinal fluid shunts, and implantable central venous access devices.

DETAILED DESCRIPTION

Figure 1A:
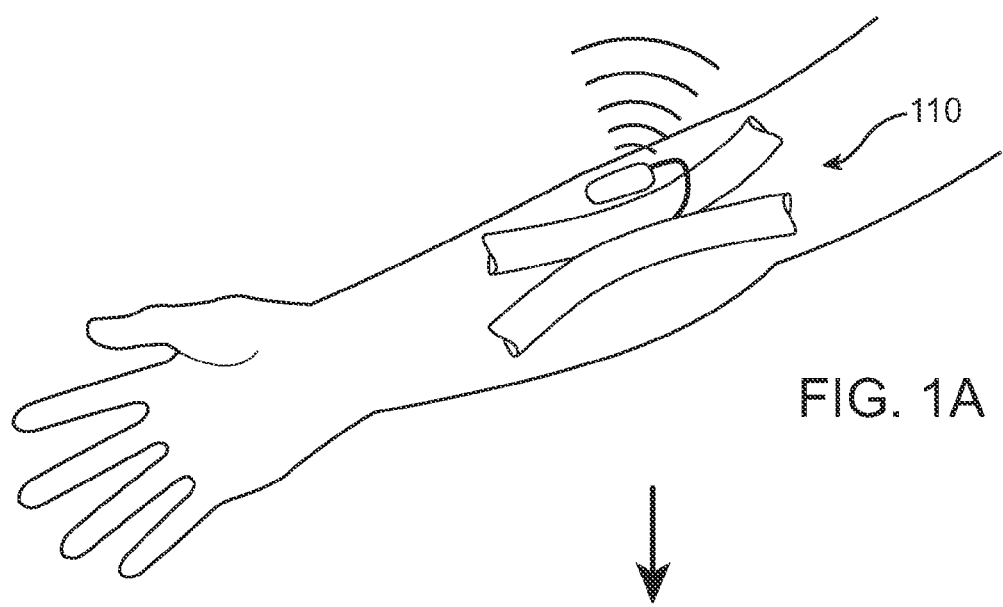
FIGS. 1A and 1B show an embodiment of the invention in which the fluid transport structure is an arteriovenous fistula.

Implantable devices for evaluating body-associated fluid transport structures and methods for using the same are provided. In some instances, the implantable devices include an elongated structure with at least one hermetically sealed integrated circuit sensor stably associated therewith and a transmitter. The devices find use in a variety of different applications, including monitoring the function of various types of body-associated fluid transport structures, such as arteriovenous fistulae, vascular grafts, catheters, cerebrospinal fluid shunts, and implantable central venous access devices. Devices Implantable fluid flow evaluation devices in accordance with invention include an elongated structure with at least one stably associated hermetically sealed integrated circuit sensor. The elongated structure is configured to position the hermetically sealed integrated circuit sensor in a sensing relationship with fluid flowing inside of the body-associated fluid transport structure of interest. Specifically, a sensing element (such as an electrode) that is outside of the hermetically sealed components of the sensor such that it can be exposed to body fluid is placed in sensing relationship with fluid flowing inside of the body-associate fluid transport structure. The fluid transport structure evaluation devices of the invention allow intermittent or continuous assessment of flow and/or characteristics of the fluid in body-associated fluid transport structures. The fluid flow evaluation devices can alert patients and caregivers to problems or complications arising within a particular fluid transport structure, such that corrective or preventative measures can be taken if desired.

By "implantable device" is meant a device that is configured to be at least partially if not wholly positioned in a living body. Implantable devices may be configured to maintain functionality when present in a physiological environment, including a high salt, high humidity environment found inside of a living body, for two or more days, such as one week or longer, four weeks or longer, six months or longer, one year or longer, including five years or longer. In some instances, the implantable devices are configured to maintain functionality when implanted at a physiological site for a period ranging from one to eighty years or longer, such as from five to seventy years or longer, and including for a period ranging from ten to fifty years or longer. The dimensions of the implantable devices of the invention may vary. However, because the implantable devices are implantable, the dimensions of certain embodiments of the devices are not so big such that the device cannot be positioned in an adult human.

By "fluid transport structure" is meant a structure through which a body-associated fluid flows, such as blood, cerebrospinal fluid, urine, bile, etc., as well as fluid that is administered to or withdrawn from a body, such as blood products, intravenous fluids, fluids containing medication or other active agents, dyalisates, etc. The fluid transport structure can be naturally occurring, surgically created, or synthetic. Fluid transport structures with which devices of the invention may be used are collectively referred to herein as body-associated fluid transport structures, and include, but are not limited to: blood vessels, including surgically created arteriovenous fistulae for hemodialysis, native vessel grafts, synthetic grafts, stent grafts, stents including vascular, urinary, biliary, or gastrointestinal tract stents, cerebrospinal fluid shunts, catheters, including vascular or urinary catheters, implantable central venous access devices, ducts such as bile ducts, or any other body-associated fluid transport structure.

Devices of the invention may be distinct components from the body-associated fluid transport structure of interest, or may include the body-associated fluid transport structure of interest. Accordingly, in some instances the devices are physically distinct from the body-associated fluid transport structure of interest. In yet other instances, the device may be integral with the body-associated fluid transport structure, such that part of the device is the body-associated fluid transport structure of interest.

In some instances, devices of the invention include an elongated structure which is flexible, and which is configured to bound a body-associated fluid transport structure of interest. By "bound" to a fluid transport structure is meant that the elongated structure is stably attached to the body-associated fluid transport structure such that the hermetically sealed integrated circuit sensor or sensors of the device are in a sensing relationship with fluid flowing through the fluid transport structure. Configurations can include those in which the sensors are located in the lumen, within the wall, or even outside of the fluid transport structure of interest, such as where the sensors are configured to obtain data through the fluid transport structure wall. In those instances where the elongated structure is distinct from the fluid transport structure of interest, the elongated structure can be bound to the fluid transport structure using any suitable method. Methods of interest included, but are not limited to, methods employing sutures, surgical staples, securing anchors, self-closing fasteners, or any other suitable fixation device.

Figure 1B:
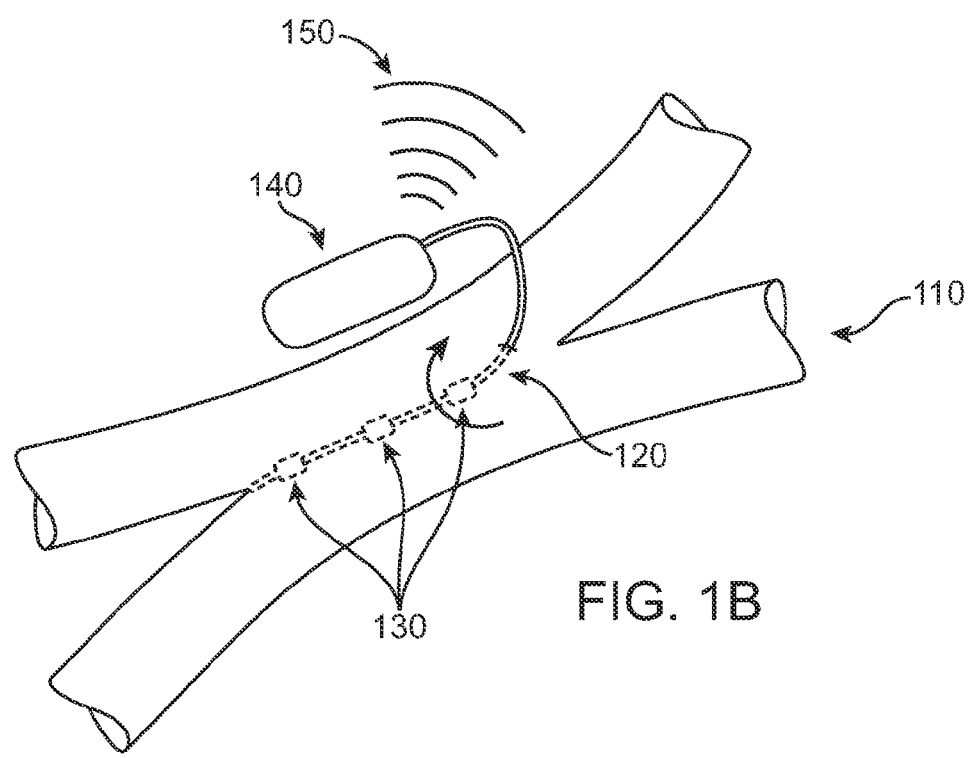

The elongated structure of the invention can be a medical carrier, such as a vascular lead structure, where such structures are generally dimensioned to be implantable and are fabricated from a physiologically compatible material. With respect to the elongated structure, a variety of different configurations may be employed, where the elongated structure in some instances is an elongated cylindrical structure having a first and a second end. The first end may include a connector element, for example, an IS-1 connector, for connecting to a control unit or analogous device. The elongated structure may include one or more lumens, for example for use with a guidewire, or for housing one or more conductive elements, for example, wires, etc. The elongated structure may further include a variety of different features as desired, for example, such as one or more securing means for attaching the elongated structure to a fluid transport structure, as discussed above.

Where the elongated structure is configured to be bound to a fluid transport structure, the diameter of the elongated structure can vary, ranging in certain instances from 1 French to 34 French, such as 1.5 French to 5 French, and including from 2 French to 3 French in diameter. The elongated structure may have a constant diameter, or it may have a diameter that varies, for example, it may taper to a smaller diameter at one or both ends. The cross-sectional shape of the elongated structure can be any suitable shape such as round, oval, hexagonal, square, etc. The length of the elongated structure will be at least partially determined by the characteristics of the fluid transport structure to which it is bound. The length may be equal to the length of the fluid transport structure to which it is bound, for example the elongated structure may be the same length as the anastomosis, or the surgically-created communication, between the artery and vein in an arteriovenous fistula as shown in FIGS. 1A and 1B. In other instances, the length may be shorter than the length of the fluid transport structure to which it is bound, for example where the fluid transport structure is a cerebrospinal fluid shunt which extends from the ventricles in the brain to the abdominal cavity. In other cases, the elongated structure may be longer than the fluid transport structure to which it is bound. In some instances, the elongated structure may range in length from 1 to 100 cm, such as from 3 to 20 cm, and including from 5 to 15 cm.

The elongated structure may be bound to the fluid transport structure in a longitudinal direction with respect to the long axis of the fluid transport structure. Alternatively, the elongated structure may be bound in a transverse direction with respect to the long axis of the fluid transport structure. In yet other instances, the elongated structure may be bound circumferentially around the fluid transport structure.

The elongated structure may be constructed of any suitable material, such as material that can be used to construct an electrical lead, or analogous medical carrier. The body of the elongated structure can be made of silicone or polyurethane, using any convenient fabrication protocol. Where desired, the elongated structures may have a protective coating, such as a polymeric coating, an anti-thrombotic coating, a coating impregnated with one or more pharmaceutical agents, etc., and may additionally have radio-opaque markers for use in locating the device with X-ray or other imaging procedures.

As mentioned above, also of interest are devices where the elongated structure is itself a fluid transport structure. In these devices, the devices include an internal passageway that is designed for fluid flow therethrough and is the body-associated fluid transport structure of interest. As with the devices described above, devices that include an integrated body-associated fluid transport structure are ones that include at least one hermetically sealed integrated circuit sensor positioned such that the sensor is in a sensing relationship with fluid in the internal passageway of the device that is the body-associated fluid transport structure. Embodiments of the implantable devices of the invention in which the elongated structure itself has an internal passageway for fluid flow can include but are not limited to: synthetic grafts, stent grafts, stents, including vascular, urinary, biliary, or gastrointestinal tract stents, implantable central venous access devices (for example as employed for delivery of medical fluids), cerebrospinal fluid shunts, catheters, including urinary catheters, hemodialysis catheters, or any other body-associated fluid transport structure.

In some instances, the device having an integrated body-associated fluid transport structure is entirely located within the body. Alternatively, the device is a structure employed to transfer of fluid between an internal body location and an exterior location. An example of such a device is a device used for hemodialysis, where blood is taken from the body of a patient who has decreased or absent kidney function in order to filter the blood with a dialysis machine before it is returned to the patient. In the types of devices, the device and integrated body-associated fluid transport structure is partially inside the body and partially outside of the body.

For devices where the elongated structure is itself a fluid transport structure, such structures are generally dimensioned to be at least partially implantable and are fabricated from a physiologically compatible material. A variety of different configurations may be employed depending on the function of the fluid transport structure, where the fluid transport structure in certain embodiments includes an elongated cylindrical element having a first and second end. As above, the device may include a connector element, for example an IS-1 connector, for connecting to a control unit or analogous device. The fluid transport structure may also include one or more lumens, for example for use with a guidewire, or for housing one or more conductive elements, for example, wires, etc. The fluid transport structure may further include a variety of different functional elements as desired, for example, a securing means for securing the fluid transport structure, such as an anchor means, etc., to a target location.

For devices having an integrated fluid transport structure, the diameter of integrated fluid transport structure may vary. In some instances, the diameter of the integrated body-associated fluid transport structure of the device may range from one mm to ten cm, such as from three mm to five cm, including from one to two cm. The fluid transport structure may have a constant diameter, or it may have a diameter that varies; for example, it may taper to a smaller diameter at one or both ends. In some instances, such as with a urethral stent, an end may be coiled into a pigtail shape, for example, which is designed to secure the stent in position. The cross-sectional shape of the elongated structure of the device that includes the integrated body-associated fluid transport structure may be any suitable shape, such as round, oval, hexagonal, square, etc. The length of the fluid transport structure of the device will be determined by its intended function. As an example, the length for a synthetic graft which extends from an artery to a vein in the forearm will be the appropriate surgically determined length sufficient to connect the two vascular structures. In contrast, the length for a ventriculoperitoneal cerebrospinal fluid shunt, which extends from the ventricles in the brain to the abdomen will be of a sufficient length to cross the distance between the two structures. As such, the length of the elongated structure which includes the body-associated fluid transport structure may range from one to one hundred cm, such as from three to twenty cm, including five to fifteen cm.

The devices may be constructed of any material suitable for the function of the body-associated fluid transport structure of the device, such as material that can be used to construct a graft, a stent, a catheter, etc. The body of the integrated body-associated fluid transport structure can be made of polyethylene terephthalate, polytetrafluroethylene (PTFE), latex, silicone, stainless steel, titanium alloys such as nickel-titanium or other suitable metal alloys, hydrogels, polyethylene and polyurethane, etc., using any convenient fabrication protocol. Where desired, the fluid transport structures may have a protective coating, such as a polymeric coating, an anti-thrombotic coating, a coating impregnated with one or more pharmaceutical agents, etc., and may additionally have radio-opaque markers for use in locating the device with imaging procedures, such as X-ray imaging procedures.

As summarized above, devices of the invention (whether or not they include an integrated body-associated fluid transport structure) have at least one hermetically sealed integrated circuit sensor. As reviewed above, the at least one hermetically sealed integrated circuit sensor is present in the device in a manner sufficient to position the sensor in sensing relationship with a fluid present in the body-associated fluid transport structure of interest. As discussed above, in some embodiments the device is bound to a body-associated fluid transport structure, and in other embodiments, the body associated fluid transport structure is an integral part of the device.

As the sensors are in a sensing relationship with fluid in the fluid transport structure of interest, the sensors have a sensing component (such as an electrode) that may be positioned in the lumen of the fluid transport structure of interest. Alternatively, the sensors have a sensing component that may be positioned within the wall of the fluid transport structure of interest. In yet other device configurations, the sensors may have a sensing component that is positioned on the outside of the fluid transport structure, for example where the sensors are configured to obtain data through a wall of the fluid transport structure of interest.

The hermetically sealed integrated circuit sensor or sensors of the devices can be placed at any suitable location of the device. Where the devices include elongated structures which may either bound the body-associated fluid transport structure of interest or include the body-associated fluid transport structure of interest (as reviewed above), the sensor or sensors may be positioned along the length of the elongated structure, as desired.

Hermetically sealed integrated circuit sensors that find use in devices of the invention are structures that include an integrated circuit element which is hermetically sealed in a hermetic sealing structure and one or more exposed sensing elements which are in electrical communication with the hermetically sealed integrated circuit component, but are not sealed in the hermetic sealing structure. The sensor elements are configured to sense a device parameter of interest.

The hermetic sealing structure is configured to protect the integrated circuit element from the implanted environment of the sensor, such that the integrated circuit sensor element remains functional for extended periods of time when implanted in a living body. The hermetic sealing structure may vary, as described in greater detail below. The hermetic sealing structure may include at least one barrier structure, such as a thick layer of material, where the structure may be configured to provide a cavity that can house one or more components of interest. Alternatively, the structure may be configured to conform to the configuration of the one or more components that are to be sealed by the structure, such that no cavity is defined by the structure and the component or components sealed thereby. The barrier is one that is sufficient to prevent passage of a critical amount of one or more molecules of interest. Molecules of interest include water molecules, as well as body-associated ions. The critical amount whose passage is prevented is an amount that adversely affects the functioning (such as by corrosion) of the sealed components over the intended lifetime of the sensor.

The sensors of the invention include an integrated circuit element. Integrated circuit elements of the invention are constructs that include circuitry components and a solid support. The solid support may be small, for example where it is dimensioned to have a width ranging from 0.01 mm to 100 mm, such as from 0.1 mm to 20 mm, and including from 0.5 mm to 2 mm; a length ranging from 0.01 mm to 100 mm, such as from 0.1 mm to 20 mm, and including from 0.5 mm to 2 mm, and a height ranging from 0.01 mm to 10 mm, including from 0.05 mm to 2 mm, and including from 0.1 mm to 0.5 mm. The solid support element may take a variety of different configurations, such as but not limited to: a chip configuration, a cylinder configuration, a spherical configuration, a disc configuration, etc., where a particular configuration may be selected based on intended application, method of manufacture, etc. While the material from which the solid support is fabricated may vary considerably depending on the particular device for which the sensor is configured for use, in certain instances the solid support is made up of a semiconductor material, such as silicon.

As summarized above, the sensors include one or more circuit elements associated with the solid support, where the circuit elements make up an integrated circuit component. Integrated circuit components of the sensors may include a number of distinct functional blocks, i.e., modules. In some instances, the circuits include at least the following functional blocks: a power extraction functional block; an energy storage functional block; a sensor functional block; a communication functional block; and a device configuration functional block.

Within a given sensor, at least some of, e.g., two or more, up to and including all of, the functional blocks may be present in a single integrated circuit. By single integrated circuit is meant a single circuit structure that includes all of the different desired functional blocks for the device. In these types of sensors, the integrated circuit is a monolithic integrated circuit that is a miniaturized electronic circuit that may be made up of semiconductor and passive components that has been manufactured in the surface of a thin substrate of semiconductor material. Sensors of the invention may also include integrated circuits that are hybrid integrated circuits, which are miniaturized electronic circuits constructed of individual semiconductor devices, as well as passive components, bonded to a substrate or circuit board.

As mentioned above, integrated circuit sensors of the invention are ones that include a sealing element (referred to also as a hermetic sealing structure) that seals the integrated circuit from the implanted environment so that the sensor maintains functionality, at least for intended lifespan. The nature of the sealing element may vary, so long as it maintains the functionality of the sensor in the implanted environment for the desired period of time, such as one week or longer, one month or longer, one year or longer, five years or longer, ten years or longer, twenty-five years or longer, forty years or longer.

In some instances, the sealing element is a conformal, void-free sealing layer, where the sealing layer is present on at least a portion of the outer surface of the integrated circuit component (described above). In some instances, this conformal, void-free sealing layer may be present on substantially all of the outer surfaces of the integrated circuit component. Alternatively, this conformal, void-free sealing layer may be present on only some of the surfaces of the integrated circuit, such as on only one surface or even just a portion of one surface of the integrated circuit component. As such, some sensors have an integrated circuit component completely encased in a conformal, void free sealing layer. Other sensors are configured such that only the top surface of an integrated circuit component is covered with the conformal, void-free sealing layer.

The conformal, void-free sealing layer may be a "thin-film" coating, in that its thickness is such that it does not substantially increase the total volume of the integrated circuit structure with which it is associated, where any increase in volume of the structure that can be attributed to the layer may be 10% or less, such as 5% or less, including 1% or less by volume. In some instances, the seal layer has a thickness in a range from 0.1 to 10.0 µm, such as in a range from 0.3 to 3.0 µm thick, and including in a range 1.0 µm thick.

The seal layer may be produced on the integrated circuit component using any of a number of different protocols, including but not limited to planar processing protocols, such as plasma-enhanced-chemical-vapor deposition, physical-vapor deposition, sputtering, evaporation, cathodic-arc deposition, low-pressure chemical-vapor deposition, etc.

Additional description of conformal, void-free sealing layers that may be employed for sensors of the invention is provided in PCT application Ser. No. PCT/US2007/009270 published under publication No. WO/2007/120884 , the disclosure of which is herein incorporated by reference.

Also of interest as sealing elements are corrosion-resistant holders having at least one conductive feedthrough and a sealing layer; where the sealing layer and holder are configured to define a hermetically sealed container the encloses the integrated circuit component. The conductive feedthrough may be a metal, such as platinum, iridium etc., an alloy of metal and a semiconductor, a nitride, a semiconductor or some other convenient material. In some instances, the corrosion-resistant holder comprises silicon or a ceramic. While dimensions may vary, the corrosion-resistant holder may have walls that are at least 1 µm thick, such as at least 50 µm thick, where the walls may range from 1 to 125 µm, including from 25 to 100 µm. The sealing layer may be metallic, where metals of interest include noble metals and alloys thereof, such as platinum and platinum alloys. Dimensions of the sealing layer may also vary, ranging in some instances from 0.5 µm thick or thicker, such as 2.0 µm thick or thicker, and including 20 µm thick or thickness, where sealing layer thicknesses may range from 0.5 to 100 µm, such as from 1 to 50 µm. In certain configurations, the structure further includes an insulative material present in the hermetically sealed volume. In some cases, the hermetically sealed volume ranges from 1 pl. to 1 ml.

In some instances, the in-vivo corrosion-resistant holder is a structure configured to hold an integrated circuit component that the integrated circuit component is bounded on all but one side by the walls of the holder. For example, the holder may include side walls and a bottom, where the holder may have a variety of different configurations as long as it contains the integrated circuit component in a manner such that the component is held in a volume bounded on all but one side. Accordingly, the shape of the holder may be square, circular, ovoid, rectangular, or some other shape as desired.

Additional description of corrosion resistant holders that may be employed for sensors of the invention is provided in PCT application Ser. no. PCT/US2005/046815 published under publication No. WO/2006/069323, the disclosure of which is herein incorporated by reference.

The hermetically sealed integrated circuit sensors of the invention may also include an external sensing component that is outside of the sealing element and connected to the integrated circuit component of the sensor by one or more conductive vias or feed-throughs. The sensing component may vary depending on the particular structure, where in certain instances the sensing component is an electrode. Where the sensing components are electrodes, the electrodes may be fabricated from a variety of different materials, including but not limited to platinum-iridium and coated with titanium-nitride or iridium-oxide, or any other material suitable for use in a human body. The vias may be any structure that provides electrical communication between integrated circuit component and the external sensing component. The vias may be made up of a corrosion-resistant conductor element and may have a variety of formats, such as a weld tab having a portion that extends through an opening or void in the sealing element to electrically contact the circuitry layer.

The hermetically sealed integrated circuit sensors of the device may vary greatly depending on the particular parameter of interest for which they are designed to sense. As reviewed in greater detail below, parameters of interest include both fluid transport structure parameters, which include parameters that indicate functioning of the transport structure, flow parameters of the fluid through the transport structure, and the like. The parameters may vary greatly, including but not limited to temperature, flow velocity, structural integrity, and the like. The sensors may be configured to sense data from which the parameter of interest may be derived using any combination of hardware and software components as desired.

Sensors that may be configured as hermetically sealed integrated circuit sensors of the inventions include, but are not limited to, those sensors as described in PCT application Ser. No. PCT/US2006/025648 published as WO/2007/028035, the disclosure of which is herein incorporated by reference.

While devices of the invention may have a single hermetically sealed integrated circuit sensor, the devices may also include two or more hermetically sealed integrated circuit sensors, such as three or more, four or more, five or more, and even six or more hermetically sealed integrated circuit sensors. In embodiments with two or more hermetically sealed integrated circuit sensors, the sensors can be separated from each other by various distances, e.g., a distance of 1 mm to 50 cm, such as 5 mm to 10 cm. Where desired, the two or more hermetically sealed integrated circuit sensors can be separated from each other by a distance of 1 mm or more, such as 5 mm or more, 10 mm or more, including 15 mm or more, or 20 mm or more.

Where desired, devices of the invention also include a transmitter component that is distinct from the elongated structure component. The transmitter is configured to transmit data obtained from the one or more sensor elements of the device to a location remote from the device. By "remote from" is meant that the location to which data are transmitted is one that is distinct from the device, where the location may be another location of the subject (internal or external) or an extra-corporeal location. The transmitter can be located at a distance from the at least one integrated circuit sensor. The distance between the transmitter and the closest integrated circuit sensor may vary, and may be 5 mm or longer, such as 10 mm, 15 mm, 25 mm, 50 mm or 100 mm or longer. In some configurations, the transmitter is positioned at one end of the elongated structure of the device. The transmitter may be part of a control unit structure that includes the transmitter present inside a housing, where one or more additional components may be present in the housing.

Within a device of the invention, electrical communication between the one or more sensors and the transmitter may be provided by a number of different approaches. For example, each sensor may include its own set of one or more signal conductors (such as wires) to provide the desired connection. Alternatively, at least two or more hermetically sealed integrated circuit sensors of the device are electrically connected to the transmitter by a common signal conductor. For example, multiplex approaches may be employed, such as those described in PCT application Ser Nos. PCT/US2003/039524 published as WO/2004/052182, PCT/US2005/031559 published as WO/2006/029090, and PCT/US2005/046811 published as WO/2006/069322, the disclosures of which are herein incorporated by reference.

In some cases, the transmitter includes a processor. The processor can be configured to process data, such as fluid transport structure data, that are obtained from the one or more sensors of the device to determine a parameter of interest, such as a fluid transport structure parameter. The processor may be configured to perform any number of additional desirable functions, including but not limited to data storage, device operation, and the like.

Sensors of device of the invention are configured to obtain data of interest, where the data may vary. Of interest are fluid flow data and fluid transport structure specific data, which are collectively referred to herein as fluid transport structure data. Fluid flow data of interest are data that are related to fluid flowing through the fluid transport structure of interest, such as data the can be used to determine fluid flow velocity, fluid temperature, fluid pressure, and the like. By "fluid transport structure specific data" is meant information about the fluid transport structure itself, such as but not limited to data that may be employed to determine temperature of the fluid transport structure, structure integrity of the device, motion of the device, and the like.

Where desired, raw data may be processed by a processor (either present in a component of the device or remote from the device) to determine a fluid transport structure parameter. By "fluid transport structure parameter" is meant a measurement, characteristic or indicator that is derived from fluid transport structure data which reflects or evaluates the status or condition of the fluid transport structure. Conditions that can be evaluated or measured include conditions such as the functionality of the fluid transport structure. For example, the impedance can be detected at various electrodes, and a fluid transport structure parameter calculated which indicates if the flow is decreased or absent in the transport structure of interest, such as a catheter or blood vessel. Alternatively, the fluid transport structure parameter can be a measure of a complication, such as infection. For example, an increased temperature of the fluid, or of the fluid transport structure, may indicate either a systemic infection, or a local infection of the fluid transport structure. The fluid transport structure parameter can also be a measure of trauma to the fluid transport structure, for example, if the sensor is an accelerometer. In some instances, the fluid transport structure parameter can be a measure not directly related to the fluid transport structure itself but one that can be useful in the treatment of a patient. For example, an accelerometer in the fluid transport structure can determine patient compliance with an exercise program.

Devices of the invention may include, where desired, a number of additional components of interest. In some instances, the devices include at least one hermetically sealed ultrasound reflector. Hermetically sealed ultrasound reflectors of interest are those that are visible with an ultrasound probe, and therefore provide a readily identifiable marker for the device with which they are associated. An ultrasound reflector may therefore be used to locate an implantable device of the invention, or any other implantable device of interest. Ultrasound reflectors incorporated into implanted medical devices of the invention can also assist in the location of the edges of body-associated fluid transport structures of interest, such as implanted central venous access devices, grafts or other implanted polymeric or plastic devices including but not limited to cerebrospinal fluid shunts, urinary stents, etc. In some instances, hermetically sealed ultrasound reflectors of the invention can be an integral part of an implantable medical device, and in other cases the hermetically sealed ultrasound reflectors of the invention can be bound to a part of an implantable device.

Figure 6A:
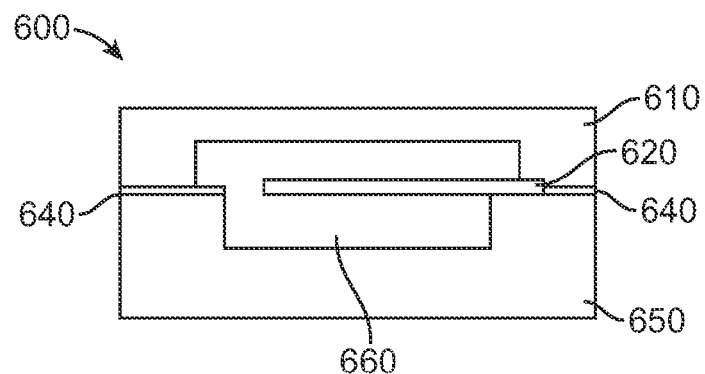
FIGS. 6A-H provides a view of a hermetically sealed ultrasound reflector according to various embodiments of the invention.

FIGS. 6A-H show various configurations of the ultrasound reflector that can be used with the devices of the subject invention. The resonator component can be housed in a hermetically sealed structure, such as a corrosion-resistant holder as described above. The ultrasound reflector can be fabricated on a substrate with a cavity, for example, as shown in FIG. 6A. FIG. 6A is a cross-sectional view of ultrasound reflector 600, with cavity 660 located between substrate 650 below and cap 610 above. Resonator 620 is suspended in cavity 660. The cavity 660 can be formed with standard Micro-Electro-Mechanical Systems (MEMS) fabrication techniques, including but not limited to chemical etching or reactive ion milling. Cavity 660 can be provided at vacuum or at air pressure, as best suits a specific application or manufacturing process. Where desired, the cavity may be filled with a soft material that allows the resonator(s) to vibrate in response to an applied ultrasound field, similar to the function of a tuning fork. The resonator can be fabricated by any suitable process, such as a sputtering, plating, or cathodic arc deposition process, etc. The resonator component can be made of tungsten, rhenium, a tungsten-rhenium compound, or any other suitable high modulus alloy or material. The resonator can, in some instances, be fabricated from the substrate material.

Figure 6B:
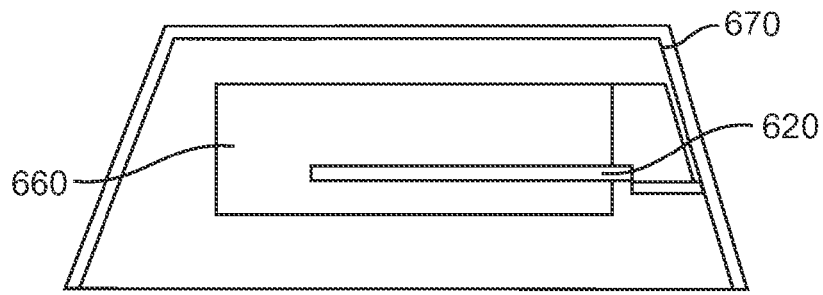

The ultrasound reflector can be sealed with seal 640, such as a glass seal, or a seal created with any other suitable MEMS technique. The ultrasound reflector can also have additional materials deposited on it to seal the edges, as shown in FIG. 6B. Sealing materials 670 that can be used to seal the edges of the ultrasound reflector include but are not limited to silicone carbide, silicone nitride, metals such as platinum, tungsten, gold, or alloys or compounds thereof. The metals can be deposited with a cathodic arc or other deposition process. In some instances, the deposited metal can be radiopaque, so that the material is visible on an x-ray.

Figure 6C:
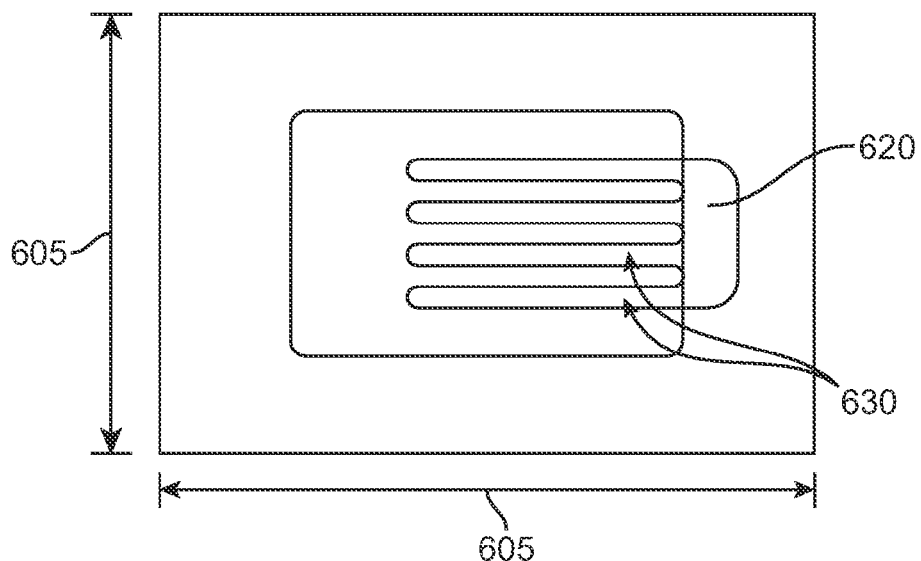

FIG. 6C is a top view of the substrate and resonator, showing the length and width 605 of the substrate, which in this example are each 0.5 mm or less. Resonator 620 can have "arms" 630 which resonate with applied ultrasound waves, and reflect a signal back to the detector allowing location of the device.

Figure 6D:
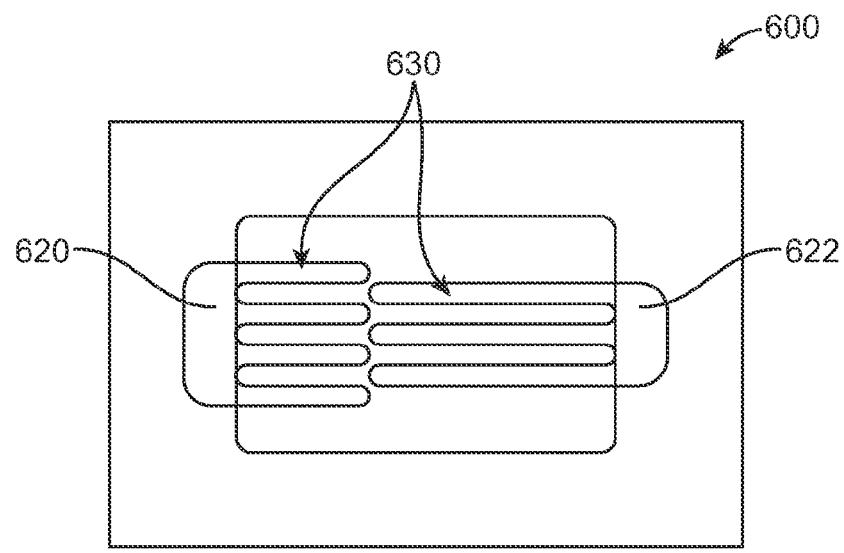

In some configurations, the ultrasound reflector device can have one resonator with multiple resonating arms, shown as 630 in FIG. 6C. In some instances, the ultrasound reflector 600 may have more than one resonator where each resonator responds to a different frequency, as shown in FIG. 6D. FIG. 6D shows resonators 620 and 622, each with multiple resonating arms 630. In this configuration, resonators 620 and 622 are of different sizes and configurations, and the arms of resonator 620 resonate at a different frequency than the arms of resonator 622. In some cases, the ultrasound reflector device can have three or more resonators, or four or more resonators, etc. Each resonator can also vary in the number of arms it has, for example a resonator may have two or more, or three or more, or four or more, etc. arms on each resonator.

Figure 6E:
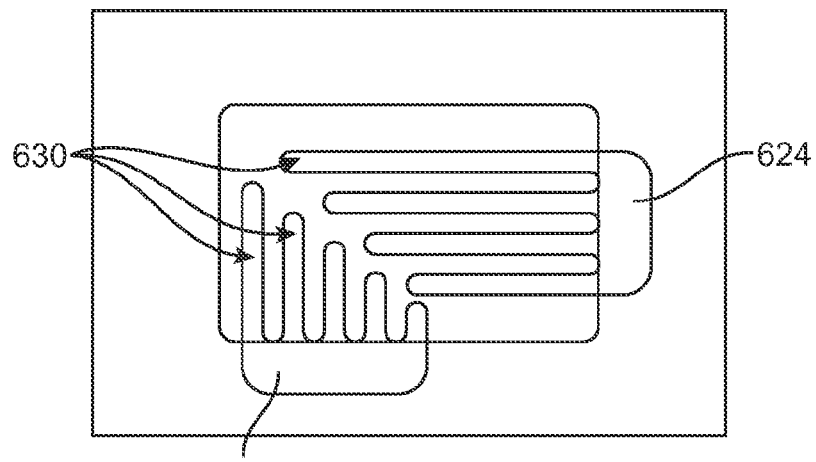

As discussed above, the ultrasound reflector 600 may include more than one resonator, as shown in FIG. 6D. FIG. 6E illustrates another example with two resonators 624 and 626, where each resonator has multiple resonating arms 630, where the resonating arms are of different sizes. In this configuration, each arm 630 within an individual resonator 624 or 626 resonates at a different frequency from the other arms in the same resonator.

Figure 6F:
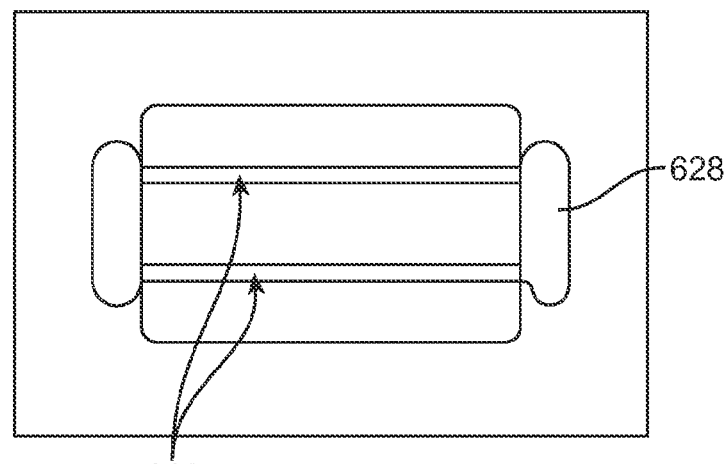

In another example, the ultrasound reflector can have a resonator 628 with arms 630 that span the length of the cavity 660, as shown in FIG. 6F.

Figure 6G:
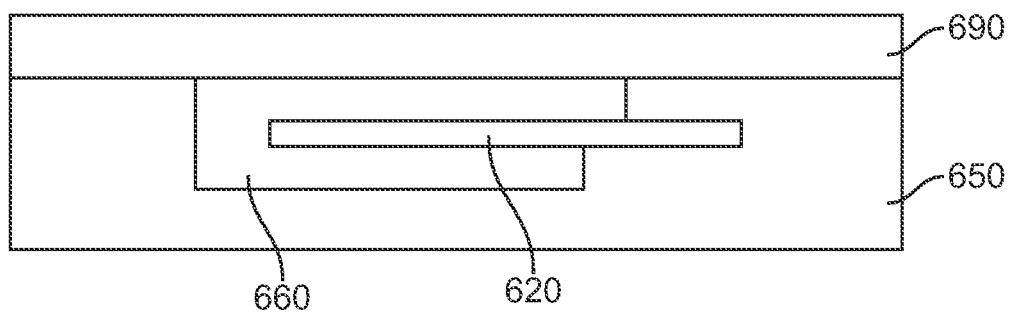
Figure 6H:
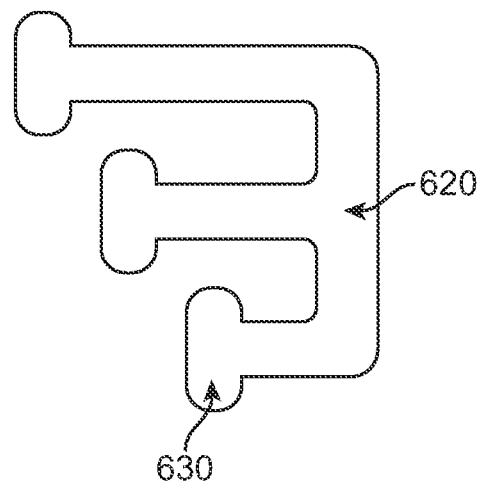

In some instances, the device can be fabricated as part of an active integrated circuit in the substrate, or it can have active circuits located above the cavity, as shown in FIG. 6G. FIG. 6G shows substrate 650 with active circuit layer 690 located above cavity 660. In some instances, the ultrasound reflector device can have a resonator or resonators that are tuned to respond to a unique frequency for purposes of identification. The resonator arms can be any suitable shape, such as "finger-like", as shown in FIGS. 6C-E, for example, or elongated rectangular, such as in FIG. 6F, or any other suitable shape such as elliptical, oval, square, etc. In addition, the resonator arms 630 can be modified in various ways to increase the function of the resonator, for example, the resonator 620 can be modified in shape to increase resonance, as shown in FIG. 6H.

The implantable devices of the subject invention may further include additional elements, such as a power source. Device power may be provided by a battery or by an external source. In some instances, lithium-type batteries can be used to power the implantable devices. External power sources may be used and can in some instances employ inductively coupled coils; or a thermo-electric cooler, for example where the device is mounted near the skin; or ultrasound energy coupled into a resonant piezo-electric component fabricated as part of the device.

Data that are collected by the implantable devices of the invention can be communicated to the patient or caregivers. Data transmission out of the body can be achieved using radiofrequency (RF) transmission by the transmitter via the Medical Implant Communication Service (MICS) or Industrial, Scientific, and Medical (ISM) bands. Alternatively, the transmitter may communicate by employing an inductively coupled power source. An external unit may include dedicated function hardware, such as a personal computer (PC), a wireless communication device such as a cellphone, etc., with the hardware and/or software required to initiate and receive the data transmissions from the implantable device.

In addition to the integrated circuit sensors and ultrasound reflectors discussed above, one or more additional physiological sensors may be included in devices of the invention, as desired. Aspects of the invention include the use of additional sensors to measure various characteristics of blood in the body, or of blood taken from or returning to the body, for example. Additional sensors can include but are not limited to: a thermistor; a thermocouple, a semiconductor device, a resistive temperature device (RTD); a light-emitting diode (LED) and a photodiode combined into a pulse oximeter, to measure blood oxygenation; a magnetic susceptibility sensor to measure anemia, as disclosed for example in published U.S. Patent Application No. 2001/0029329; a pressure sensor, such as a capacitive or piezo-resistive device which can measure blood pressure; or a cuff with strain gauges that can be placed around a vessel or catheter to measure pressure deflections.

Examples of the devices according to the invention are shown in FIGS. 1 to 5. In FIGS. 1A and B, an embodiment of the implantable device for use with a surgically-created arteriovenous fistula 110 is shown. The arteriovenous fistula is a surgically-created communication between an artery and a vein, to create a site used for vascular access patients with kidney failure who require hemodialysis in order to filter the blood and remove toxins. FIG. 1A shows the forearm of a subject containing the arteriovenous fistula. FIG. 1B is an enhanced view of the fistula which includes the implantable device of the subject invention. In this example, an elongated structure 120 having three hermetically sealed integrated circuit sensors 130 has been bound to the body-associated fluid transport structure of interest, which is arteriovenous fistula 110. In this device, the long axis of the elongated structure 120 where the structure is bound to the surgically created fistula is transverse to the direction of blood flow through the fistula, as the blood flows from the high pressure arterial system to the lower pressure venous system.

The transmitter is contained within the portion of the implantable device that includes a control unit 140, which can also have a power source. The sensors 130 can each be hard-wired to the transmitter with their own signal conductor, or can be connected to the transmitter with a common conductor, such as with a multiplex system, with addressable integrated circuits at each sensor location. The sensors 130 are located inside the fistula, such that they are in a sensing relationship with the fluid in the arteriovenous fistula. The sensors in this instance may be configured to sense characteristics of fluid flow inside the fistula, such by measuring impedance between at least two of the sensors. The sensors can also measure characteristics of the blood in the fistula, for example, temperature or oxygen content. The wireless transmission of information such as fluid transport structure data to an external unit is shown as element 150.

Figure 2A:
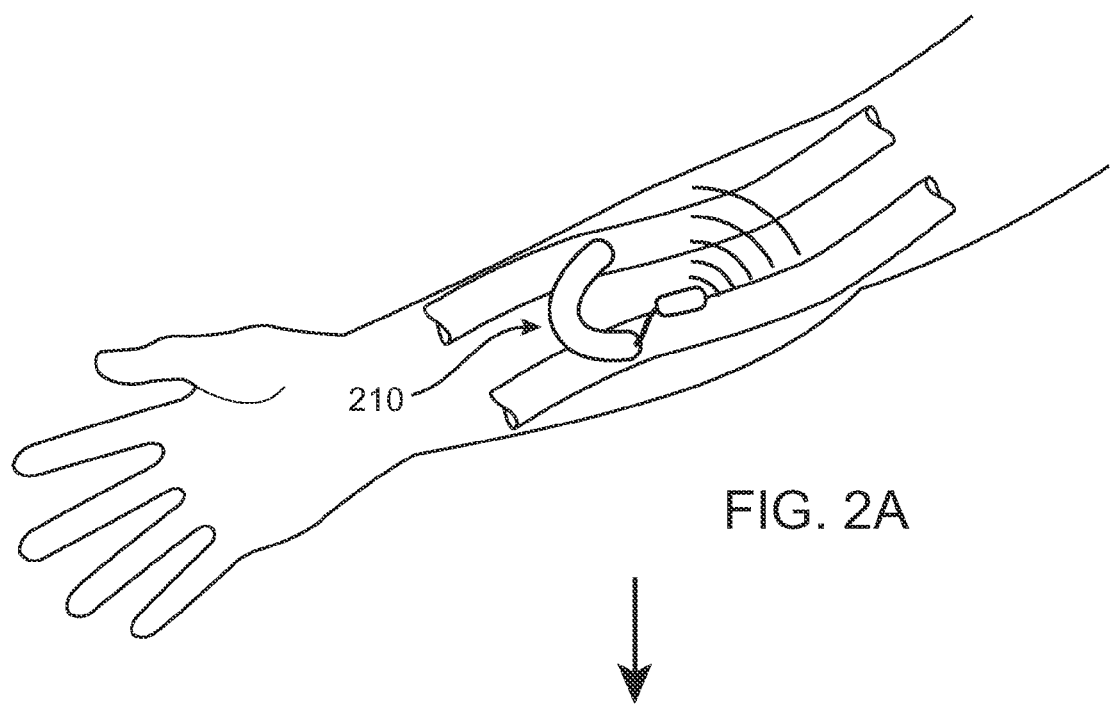
FIGS. 2A and 2B show an embodiment of the invention in which the fluid transport structure is a graft.
Figure 2B:
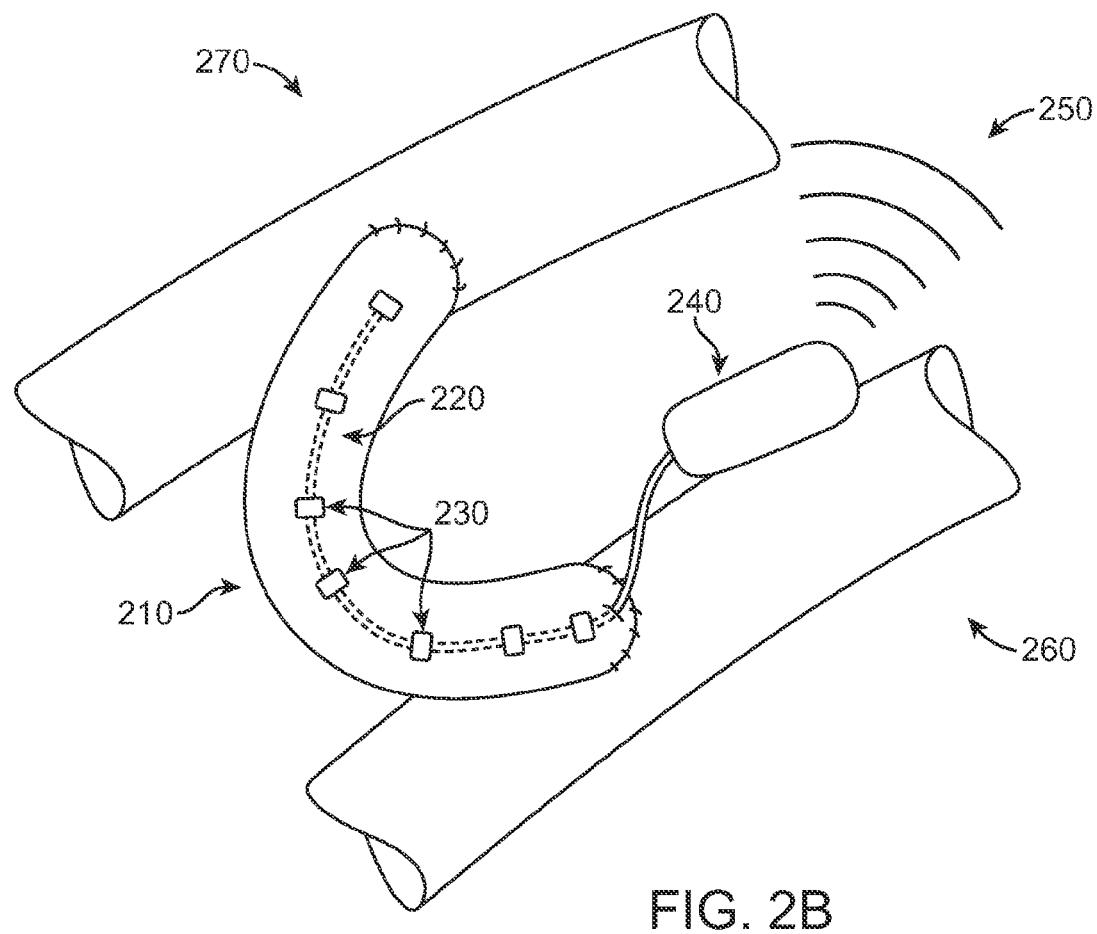

In FIGS. 2A and B, another embodiment of the implantable device for use with a graft for hemodialysis 210 placed between artery 260 and vein 270 in the forearm is shown. FIG. 2A shows the forearm of a subject containing the graft. FIG. 2B is an enhanced view of the graft which includes the implantable device of the subject invention. In this example, an elongated structure 220 having seven hermetically sealed integrated circuit sensors 230 has been bound to the fluid transport structure, in this case the graft 210. In this instance the elongated structure 220 is oriented in a longitudinal direction with respect to the long axis of the graft located between an artery and vein of the forearm. The transmitter is contained within the portion of the implantable device that includes a control unit in a housing 240, which can also have a power source. As in FIGS. 1A and 1B, the sensors 230 can each be hardwired to the transmitter with their own signal conductor, or can be connected to the transmitter with a common conductor, such as with a multiplex system, with addressable integrated circuits at each sensor location. The sensors 230 are located inside the graft, such that they are in a sensing relationship with the fluid in the graft. The wireless transmission of data such as fluid transport structure data to an external unit is shown as element 250.

Figure 3A:
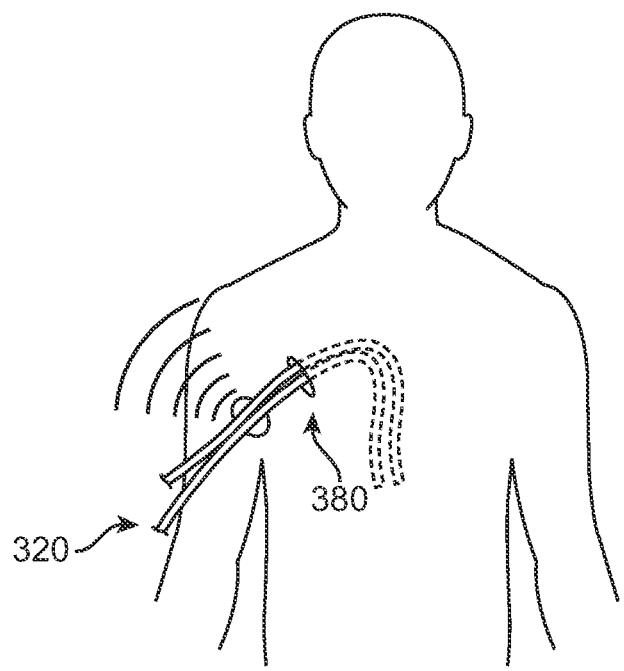
FIGS. 3A and 3B show an embodiment of the invention in which the fluid transport structure is hemodialysis catheter.
Figure 3B:
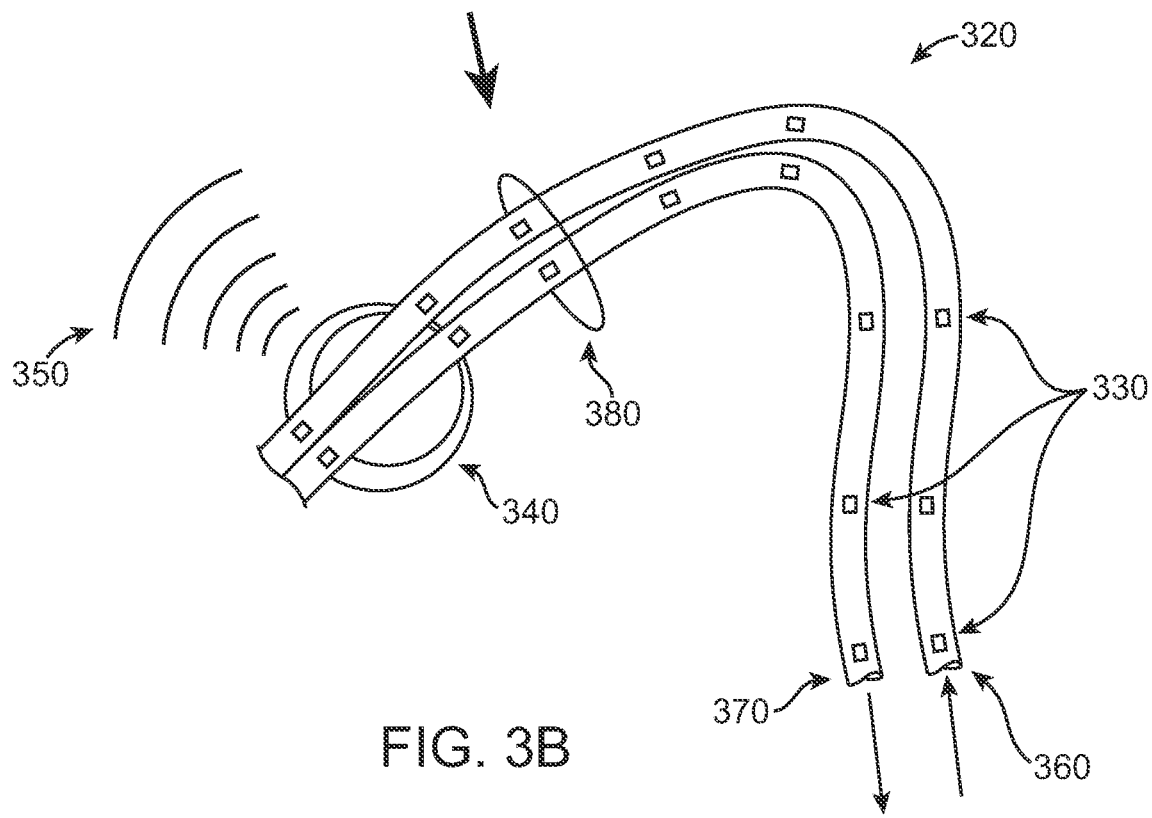

An embodiment of an implantable device where the elongated structure comprises a fluid transport structure, such as a hemodialysis catheter 320, is shown in FIGS. 3A and 3B. FIG. 3A shows a hemodialysis catheter 320 placed in the subclavian vein, through incision site 380. FIG. 3B is an enhanced view of the catheter 320, which has two lumens; one lumen 360 is for blood drawn up into the dialysis machine, and the other lumen 370 is for the return of the filtered blood. In this device, the catheter 320 has multiple sensors 330 inside both lumens. The transmitter is contained within control unit 340, which in this example is located outside of the body. The sensors 330 can each be hardwired to the transmitter with their own signal conductor, or can be connected to the transmitter with a common conductor, such as with a multiplex system. The wireless transmission of data such as fluid transport structure data to an external unit is shown as element 350.

Figure 4A:
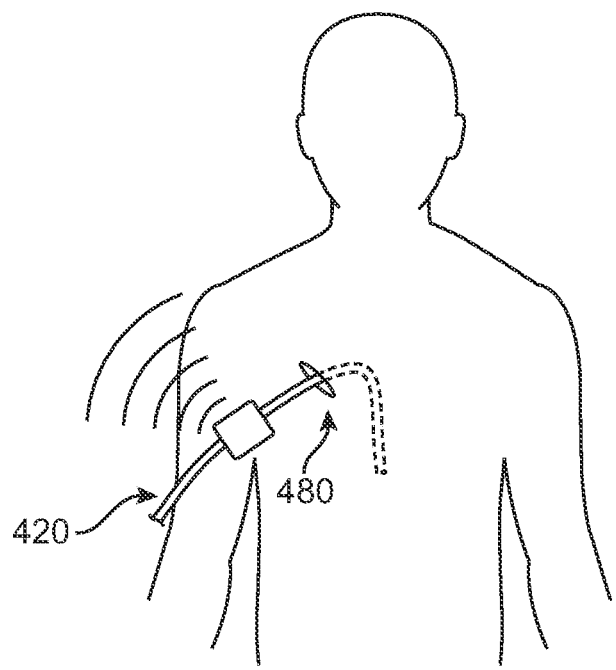
FIGS. 4A and 4B show an embodiment of the invention in which the fluid transport structure is a hemodialysis catheter.
Figure 4B:
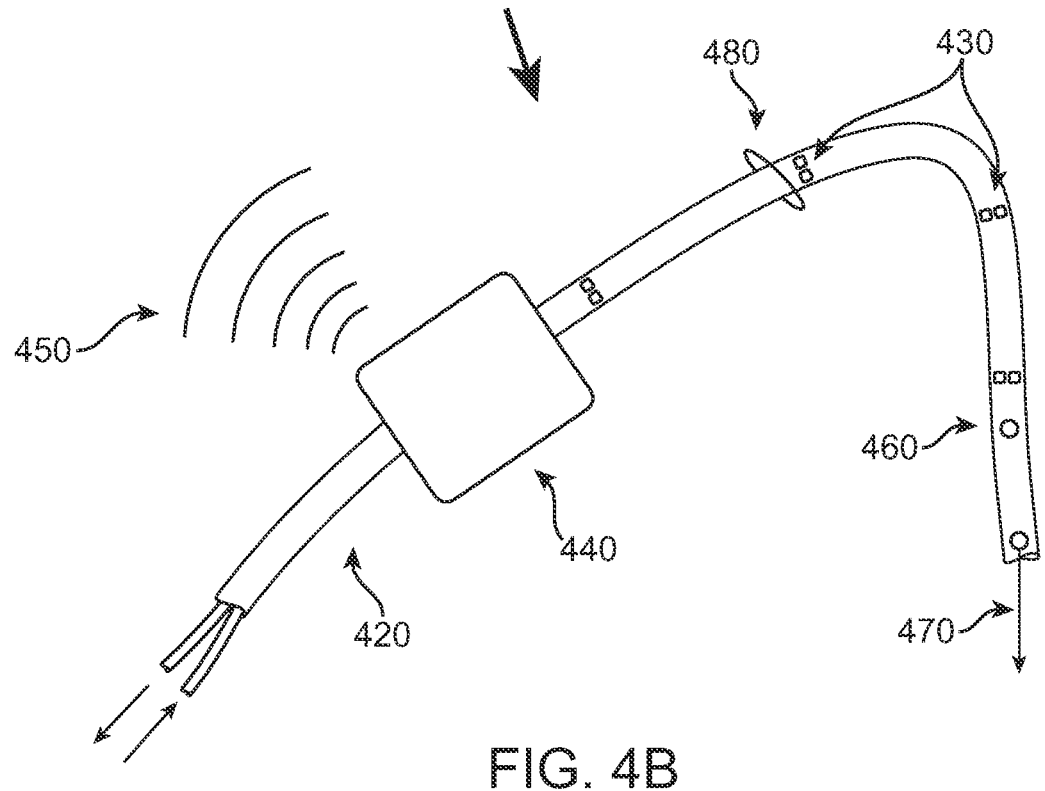

Another configuration of the implantable device where the elongated structure comprises a fluid transport structure is shown in FIGS. 4A and B. FIG. 4A shows a hemodialysis catheter 420 placed in the subclavian vein, through incision site 480. FIG. 4B is an enhanced view of the catheter 420, which has an opening 460 for blood to be drawn up into the catheter, with catheter end 470 for the return of the filtered blood. The catheter 420 has multiple sensors 430 inside the lumen. The transmitter is contained within control unit 440, which is located outside of the body. The sensors 430 can each be hardwired to the transmitter with their own signal conductor, or can be connected to the transmitter with a common conductor. The wireless transmission of data such as fluid transport structure data to an external unit is shown as element 450.

Figure 5A:
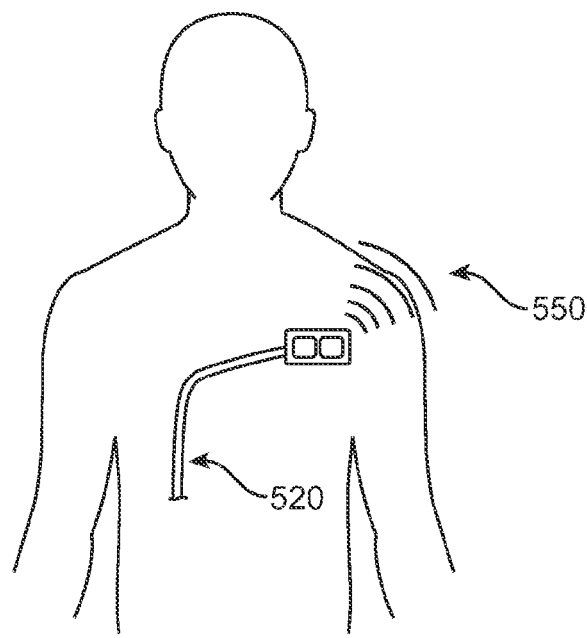
FIGS. 5A and 5B show an embodiment of the invention in which the fluid transport structure is an implantable central venous access device.
Figure 5B:
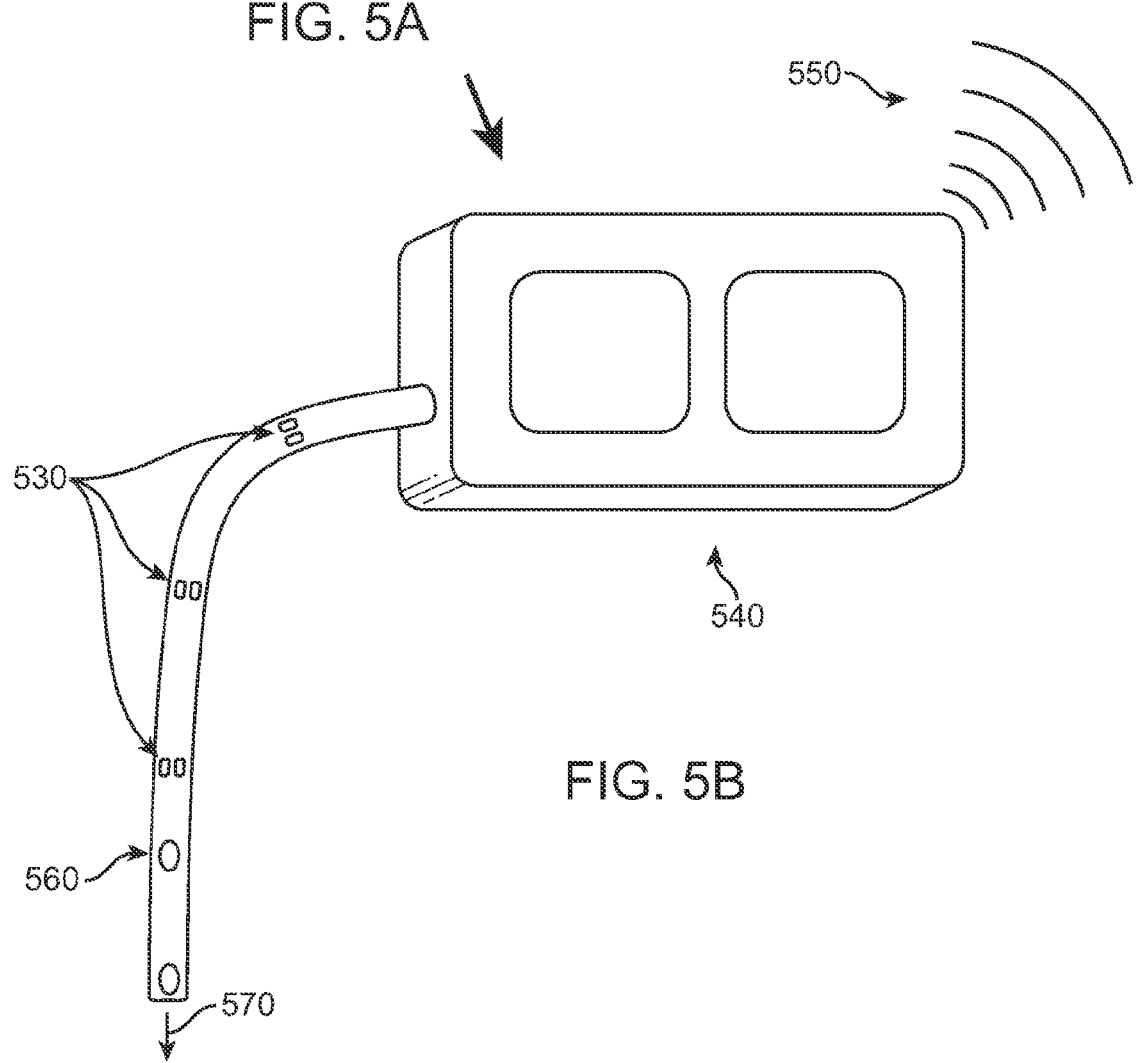

Another example of the implantable device where the elongated structure comprises a fluid transport structure is shown in the implantable central venous access device of FIGS. 5A and B. FIG. 5A shows central venous access device 520, with the catheter portion of the device placed in the subclavian vein, and a subcutaneously located port 540. FIG. 5B is an enhanced view of the central venous access device 520, which has opening 560 for blood to be drawn up into the catheter and catheter end 570 for the return of the filtered blood to the patient. The catheter portion of the device 520 has multiple sensors 530 inside the lumen. The transmitter is located within the subcutaneous port 540. Sensors 530 can each be separately hardwired to the transmitter or connected to the transmitter with a common conductor. The wireless transmission of data from subcutaneous port 540 to an external unit is shown as element 550.

In some instances, the devices of the invention are configured for detection of infection associated with a fluid transport structure of interest. In some instances, a single temperature measurement may be used as an indicator of infection, for example where the implant site is close to the body core and minimally influenced by the environment. Alternatively, a differential measurement may be used where the implant site is closer to the body surface and therefore more susceptible to influence by environmental conditions. In this case, one sensor may be placed near the access point and another sensor may be placed some distance away from the access point but at the same tissue depth. Both sensors will be influenced to the same degree by the patient's environment. In this configuration, a temperature difference observed between the two sensors used as indicator of infection at the access point, for example of infection developing from a mis-handled dialysis device or catheter.

In certain instances, the implanted devices are configured to provide detection and monitoring of fluid flow through a body-associated fluid transport structure. Instances where monitoring of fluid flow is desirable include those where the fluid transport structure is susceptible to blockage, for example blockage resulting from thrombus formation. One example of such a device includes a device that includes two or more pressure sensors spaced a distance apart from each other on the fluid transport structure. With this configuration, pressure measurements may be obtained from the sensors and any differences in the observed measurements determined. Differences in observed pressure may be employed as an indicator of blockage in the fluid transport structure. Alternatively, impedance measurements obtained from suitable spaced apart sensors may be employed to determine the presence of a blockage or flow impedance structure in the transport structure.

In certain uses, the devices are configured for trauma detection. Any implanted device can be subject to damage due to trauma, especially in ambulatory patients. For example, an implantable central venous access device used to infuse clotting factor in a child with hemophilia may be damaged if struck with a ball. An accelerometer or a Micro-Electro-Mechanical Systems (MEMS) fabricated mechanical fuse similar to the "shock watch" devices used to monitor packages during shipment can be mounted in the device. In this configuration, the fuse can be periodically interrogated, such as when an infusion is performed with a port. If the fuse is broken, a more detailed investigation can be performed to evaluate the integrity of the device.

In some instances, the devices can be configured to be used for subjects in which the recommended treatment for the underlying disease includes exercise. Incorporation of an accelerometer in the device can allow the physician attending to the patient assess compliance with an exercise program. Accelerometer data can be collected over a bandwidth of 0.5 to 2.5 Hz. The raw data may be reduced to vector magnitude units or using acti-graphs.

The devices can also be configured to be employed in embolism detection. Emboli are a serious complication that can result from damaged catheters, ports, and infusion sets. In this instance, a differential alternating current (AC) impedance measurement may be employed as means to detect embolism. Impedance can be measured using AC signals at two different frequencies. When the impedances start to diverge, this divergence may be employed as an indication that an embolus may be present in the fluid transport structure of interest.

Where desired, the devices are configured to provide for easy detection and location of the device in the body. For example, fully implanted fluid transport structures (such as the device shown in FIGS. 5A and 5B) that are configured to interact with a fluid delivery device, such as a syringe, may be configured to provide a user (such as a caregiver) with information about an optimal location on the skin surface to puncture the skin and access the port. The implanted device may include two or more hermetically sealed integrated circuit sensors, where the sensors include body exposed electrode sensor elements. When such sensors are configured to provide an electrode array, the sensors may be employed with an appropriate configured parenteral delivery system to provide a user with feedback regarding appropriate puncture location. An example of an appropriate parenteral delivery system is disclosed in PCT application Ser. No. PCT/USUS2007/015547 and published as WO/2008/008281; the disclosure of which is herein incorporated by reference. In such embodiments, an implanted device can be localized using an electrode array made up of two or more hermetically sealed integrated circuit sensors, where the system provides information to the user needed to find a good puncture side. For example, the syringe may be operated to broadcast a signal as it approaches the skin. The broadcast signal may be sensed by the hermetically sealed integrated circuit sensors and resultant data processed to identify the syringe in the x,y,z coordinate space relative to the device and access port thereof.

Systems

Aspects of the invention further include systems. Systems of the invention include a device for evaluating a fluid flow transport structure as described above. The systems may further include a receiver element configured to receive a signal transmitted from the device. The receiver may be a body-associated receiver or an extracorporeal receiver that is not in direct contact with the body. Body-associated receivers of interest include personal signal receivers, such as the personal signal receivers described in PCT Application Ser. Nos. PCT/US2008/052845 published as WO/2008/095183 and PCT/US2006/016370 published as WO/2006/116718, the disclosures of which are herein incorporated by reference. In certain instances, systems may further include an external unit, such as an extracorporeal data processing and/or communication device, which may be wired or wireless, an external power source, etc.

In some instances the systems include one or more of: a data storage element, a data processing element, a data display element, data transmission element, a notification mechanism, and a user interface, where these components of the systems are distributed among two or more distinct implanted and/or extracorporeal devices. For example, these elements may be incorporated into a signal receiver and/or present on an external unit or device, for example, a device configured for processing data and making decisions, forwarding data to a remote location which provides such activities, etc.

Systems of the subject invention can include one or more additional physiological sensors that are distinct from the hermetically sealed integrated circuit sensor or sensors of the devices of the invention. Systems that include multiple sensors can increase the likelihood of detecting a complication, and can alert a patient and/or physician to such changes before they would normally be detected. In one example, signs of infection can be assessed with one or a variety of sensors. For example, optic sensors can be employed to assess reddening of a local skin site. Soft tissue swelling and changes in pulse can be assessed by pressure sensors. A subject's activity level can be assessed with standard piezoelectric or other sensors, and the position of a subject, such as whether a subject is supine or upright can give important context to the empiric sensor data.

Methods

Also provided are methods of using the implantable devices of the invention to evaluate a body-associated fluid transport structure. Methods of invention may include employing the fluid transport structures in their conventional sense, and also include obtaining fluid transport structure data from at least one hermetically sealed integrated circuit sensor of a device of the invention.

Aspects of methods of the invention may include determining a fluid transport structure parameter, where the parameter is determined by a processor using fluid transport structure data obtained from the device for the body-associated fluid transport structure of interest. The processor employed to determine the parameter of interest from the data can be part of the device or be part of an external unit.

Methods of using the subject implantable devices also include methods of implanting the devices as described above into a subject. The methods of implanting the subject devices can include stably associated an elongated structure to a body associated fluid transport structure of interest, as for example, to an arteriovenous fistula as shown in FIGS. 1A and 1B. Stably associated the elongated structure to a body-associated fluid transport structure of interest can include, for example, surgical methods, such as suturing, that can be used when creating an arteriovenous fistula for dialysis in the forearm. Other methods for stably associated the implantable device to a fluid transport structure such as a native vessel or synthetic graft can include, but are not limited to, any suitable minimally invasive, endovascular, interventional, or endoscopic procedure. In some instances, the elongated structure can is stably associated with a body-associated fluid transport structure, such as a cerebrospinal fluid shunt or urinary catheter, before the fluid transport structure is implanted in the body.

The methods of implanting the subject devices can also include methods of implanting an elongated structure where the elongated structure itself comprises a fluid transport structure, such as the devices shown in FIGS. 3A to 5B. Methods of implanting these devices include any conventional method of implanting the fluid transport structures, such as surgical, minimally invasive, endovascular, interventional, endoscopic, or other convenient methods. For example, for implantation of an implantable central venous access device as shown in FIGS. 5A and 5B, any conventional percutaneous or cutdown method may be used to place the device in a suitable central vein such as the subclavian, internal jugular, or femoral vein, etc.

Methods of the invention also include methods of fabricating an implantable device for evaluating a body-associated fluid transport structure, which includes conductively coupling at least one hermetically sealed integrated circuit sensor and at least one signal conductor, and associating at least one sensor and at least one conductor with an elongated structure, where the elongated structure is configured to position the hermetically sealed integrated circuit sensor in sensing relationship with fluid in a body-associated fluid transport structure of interest. Any of a variety of different protocols may be employed in manufacturing devices of the invention and components thereof. For example, molding, deposition and material removal, for example, planar processing techniques, such as Micro-Electro-Mechanical Systems (MEMS) fabrication techniques, including surface micromachining and bulk micromachining techniques, may be employed. Deposition techniques that may be employed in methods of fabricating the structures include, but are not limited to: electroplating, cathodic arc deposition, plasma spray, sputtering, e-beam evaporation, physical vapor deposition, chemical vapor deposition, plasma enhanced chemical vapor deposition, etc. Material removal techniques included, but are not limited to: reactive ion etching, anisotropic chemical etching, isotropic chemical etching, planarization, for example, via chemical mechanical polishing, laser ablation, electronic discharge machining (EDM), etc. Also of interest are lithographic protocols. Of interest is the use of planar processing protocols, in which structures are built up and/or removed from a surface or surfaces of an initially planar substrate using a variety of different material removal and deposition protocols applied to the substrate in a sequential manner.

Utility

Devices and methods of the invention, for example as described above, find use in a variety of applications that involve the use of a body-associated fluid transport structure. One application in which the methods and devices of the invention find use includes the evaluation of the functionality of a body-associated fluid transport structure. This evaluation may be made up of a one-time observation or a multiple observations over a given time period, such that the evaluation is employed to monitor the functionality of a fluid transport structure over a given period of time, including up to the life span of a given body associate fluid transport structure. Evaluations of the invention may take a variety of different formats, including identification of infection, identification of any compromise in functionality of a fluid transport structure of interest, and the like.

Where desired, the data obtained using devices of the invention is employed in conjunction with data obtained from other "smart" devices, such as parenteral fluid delivery devices as described in PCT application Ser. No. PCT/USUS2007/015547 and published as WO/2008/008281; as well as ingestible event marker devices, such as those described in PCT application Ser. Nos. PCT/US2006/016370 published as WO/2006/116718 and PCT/US2008/052845 published as WO/2008/095183, the disclosures of which are herein incorporated by reference. In some instances, devices of the invention are used to track the frequency, duration, and timing of dialysis when used with compatible "smart" dialysis systems. When multiple implantable central venous access devices, or ports, are present, these can be identified using the port information systems as described in pending U.S. Patent Application Ser. No. 12/258,298 titled "Fluid Transfer Port Information System," the disclosure of which is herein incorporated by reference. Additionally, in some cases, subjective observations of the patient and caregiver, such as nausea, headache, lethargy, light headedness, can be inputted into the system as part of a complete, automatic assessment.

Applications of interest include those where specific areas of device compromise can be identified using the inventive sensing systems. For example, in the case of central nervous system (CNS) shunts, the system can identify the following areas of failure automatically and before adverse sequeli occur. Because the assessment is continuous, and can be conveyed to the patient or caregiver, early intervention is possible. In some configurations, the system can provide instructions to the patient or caregiver, such as "lay in Trendelenburg position" "pinch off valve occluder" "assume upright posture" and the like, to provide early intervention in the case of a complication. Complications which can be assessed or detected using the subject systems include but are not limited to: proximal or distal catheter or valve obstruction, decreased or absent flow, infection, disconnected components, shunt over-or under-drainage, shunt over- or under-function, hypotension, mal-positioning of a catheter or device, etc.

In certain instances, the devices may be employed by caregivers to assess compliance with maintenance procedures for a body-associated fluid transport structure of interest. A variety of fluid transport structures requires regular maintenance for optimal performance. For example, in many cases a central intravenous line needs to be flushed with heparin every thirty days if it has not been used. Similarly, CF-shunts require period pumping. Devices of the invention may be employed to record when maintenance is performed and alert when needed, e.g., to a patient a message via e-mail, voice-mail, etc.

Kits

Also provided are kits. Kits may include one or more body-associated fluid transport structure evaluation devices of the invention, such as those described above. In certain instances, the kits may also include an external unit such as a monitoring device, for example, as described above, for receiving data from a transmitter, and which may provide for communication with a remote location, for example, a doctor's office, a central facility etc., which obtains and processes data obtained about the usage of the composition. The kits may also include additional elements such as a power source, a personal signal receiver, etc.

Kits of the invention may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (that is, associated with the packaging or sub-packaging) etc. The instructions can also be present as an electronic storage data file present on a suitable computer readable storage medium, for example CD-ROM, diskette, etc. In yet other configurations, the actual instructions are not present in the kit, but directions for obtaining the instructions from a remote source, for example via the internet, are provided. As an example, a kit that includes a web address where the instructions can be viewed and/or from which the instructions can be downloaded could be provided. As with the instructions, the directions for obtaining the instructions are recorded on a suitable substrate.

Some or all components of the subject kits may be packaged in suitable packaging to maintain sterility. The components of the kit can be packaged in a kit containment element to make a single, easily handled unit, where the kit containment element, for example, box or analogous structure, may or may not be an airtight container, for example, to further preserve the sterility of some or all of the components of the kit.

It is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An implantable device comprising:
  a single lumen catheter comprising:
    an elongated flexible tubular catheter body having a proximal end, a distal end, and at least one opening formed on the elongated flexible tubular catheter body between the proximal end and the distal end, the at least one opening is configured to draw up blood into the elongated flexible tubular catheter body and the distal end is configured to return the blood; and
    a plurality of hermetically sealed integrated circuit sensors formed inside the elongated flexible tubular catheter body, the plurality of hermetically sealed integrated circuit sensors configured to sense the blood to generate data associated with the blood; and
    a subcutaneous port physically coupled to the single lumen catheter at the proximal end of the elongated flexible tubular catheter body,
  the subcutaneous port comprising:
    a transmitter communicatively coupled to the plurality of hermetically sealed integrated circuit sensors, the transmitter configured to transmit the data obtained from the plurality of hermetically sealed integrated circuit sensors to an external device.

2. The implantable device of claim 1, wherein the plurality of hermetically sealed integrated circuit sensors comprise at least two hermetically sealed integrated circuit sensors.

3. The implantable device according to claim 2, wherein the at least two hermetically sealed integrated circuit sensors are each connected to the transmitter by individual signal conductors.

4. The implantable device according to claim 2, wherein the at least two hermetically sealed integrated circuit sensors are connected to the transmitter by a common signal conductor.

5. The implantable device according to claim 1, further comprising a power source.

6. The implantable device according to claim 1, further comprising a hermetically sealed ultrasound reflector.

7. The implantable device according to claim 1, wherein the transmitter comprises a processor configured to process the data obtained from the plurality of hermetically sealed sensors.

8. A system for evaluating fluid flow, the system comprising:
  a single lumen catheter comprising:
    an elongated flexible tubular catheter body having a proximal end, a distal end, and at least one opening formed on the elongated flexible tubular catheter body between the proximal end and the distal end, the at least one opening is configured to draw up blood into the elongated flexible tubular catheter body and the distal end is configured to return the blood; and
    a plurality of hermetically sealed integrated circuit sensors formed inside the elongated flexible tubular catheter body, the plurality of hermetically sealed integrated circuit sensors configured to sense the blood to generate data associated with the blood;
    a subcutaneous port physically coupled to the single lumen catheter at the proximal end of the elongated flexible tubular catheter body,
  the subcutaneous port comprising:
    a transmitter communicatively coupled to the plurality of hermetically sealed integrated circuit sensors, the transmitter configured to transmit the data obtained from the plurality of hermetically sealed integrated circuit sensors; and
    an external unit configured to receive the data from the transmitter.

9. The system according to claim 8, wherein the external unit comprises a processor configured to process the data obtained from the transmitter.

10. The system according to claim 8, wherein the transmitter comprises a processor configured to process the data obtained from the plurality of hermetically sealed integrated circuit sensors.

11. A kit comprising:
(a) a device comprising:
(i) a single lumen catheter comprising:
an elongated flexible tubular catheter body having a proximal end, a distal end, and at least one opening formed on the elongated flexible tubular catheter body between the proximal end and the distal end, the at least one opening is configured to draw up blood into the elongated flexible tubular catheter body and the distal end is configured to return the blood; and
a plurality of hermetically sealed integrated circuit sensors formed inside the elongated flexible tubular catheter body, the plurality of hermetically sealed integrated circuit sensors configured to sense the blood to generate data associated with the blood; and
(ii) a subcutaneous port physically coupled to the single lumen catheter at the proximal end of the elongated flexible tubular catheter body,
the subcutaneous port comprising:
a transmitter communicatively coupled to the plurality of hermetically sealed integrated circuit sensors, the transmitter configured to transmit the data obtained from the plurality of hermetically sealed integrated circuit sensors; and
(b) an external unit for receiving the data from the transmitter.

12. The device according to claim 6, wherein the hermetically sealed ultrasound reflector comprises:
a substrate with a cavity;
a cap sealing the cavity; and
at least one resonator suspended in the cavity.

13. The device according to claim 12, wherein the at least one resonator is made of a high modulus alloy.

14. The device according to claim 12, wherein the at least one resonator comprises two resonators of different sizes and configurations.

15. The device according to claim 14, wherein the two resonators resonate at two different frequencies.

16. The device according to claim 12, wherein each of the at least one resonator comprises multiple resonator arms.

17. The device according to claim 16, wherein a shape of the multiple resonator arms is finger-like.

* * * * *

UNITED STATES PATENT AND TRADEMARK OFFICE
CERTIFICATE OF CORRECTION

| | | |
|---|---|---|
| PATENT NO. | : 8,419,638 B2 | Page 1 of 1 |
| APPLICATION NO. | : 12/273503 | |
| DATED | : April 16, 2013 | |
| INVENTOR(S) | : Lawrence W. Arne et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 939 days.

Signed and Sealed this
Twenty-third Day of December, 2014

Michelle K. Lee
*Deputy Director of the United States Patent and Trademark Office*